US008518637B2

(12) United States Patent
Barnes et al.

(10) Patent No.: US 8,518,637 B2
(45) Date of Patent: Aug. 27, 2013

(54) METHOD OF PROVIDING PORTABLE BIOLOGICAL TESTING CAPABILITIES

(76) Inventors: Allen C. Barnes, Shreveport, LA (US); Janice Barnes, Shreveport, LA (US)

( * ) Notice: Subject to any disclaimer, the term of this patent is extended or adjusted under 35 U.S.C. 154(b) by 319 days.

(21) Appl. No.: 13/032,396

(22) Filed: Feb. 22, 2011

(65) Prior Publication Data

US 2011/0143388 A1 Jun. 16, 2011

Related U.S. Application Data

(62) Division of application No. 11/836,541, filed on Aug. 9, 2007, now Pat. No. 7,910,361.

(60) Provisional application No. 60/822,004, filed on Aug. 10, 2006.

(51) Int. Cl.
*C12Q 1/00* (2006.01)
*C12M 1/34* (2006.01)

(52) U.S. Cl.
USPC ...... 435/4; 435/305.1; 435/288.3; 435/289.1; 435/287.2; 435/287.1; 251/336; 251/298

(58) Field of Classification Search
USPC ................ 435/305.1, 4, 287.1, 287.2, 289.1, 435/288.3; 251/336, 298
See application file for complete search history.

(56) References Cited

U.S. PATENT DOCUMENTS

| | | | |
|---|---|---|---|
| 1,337,981 | A | 4/1920 | Waggoner |
| 2,144,255 | A | 1/1939 | Carpenter |
| 2,701,229 | A | 2/1955 | Scherr |
| 2,971,892 | A | 2/1961 | Carski |
| 3,055,808 | A | 9/1962 | Henderson |
| 3,692,493 | A | 9/1972 | Terasaki |
| 3,928,136 | A | 12/1975 | Launey |
| 3,928,142 | A | 12/1975 | Smith |

(Continued)

FOREIGN PATENT DOCUMENTS

| | | |
|---|---|---|
| CA | 2 353 923 | 6/2000 |
| DE | 19631997 A1 | 2/1998 |

(Continued)

OTHER PUBLICATIONS

Examination Report for European App. No. 07 813 962.3 dated Jul. 12, 2010.

(Continued)

*Primary Examiner* — Nathan Bowers
(74) *Attorney, Agent, or Firm* — Knobbe, Martens, Olson & Bear LLP

(57) ABSTRACT

A method for providing portable biological testing capabilities free from biological contamination from an environment outside the device is provided. The method includes providing components configured to be assembled together to seal a volume against passage of biological materials between the volume and an environment outside the volume. The method further includes sterilizing the components and providing a sterilized culture medium. The method further includes assembling the components together with the sterilized culture medium within the volume. The method further includes sterilizing the assembled components by elevating the temperature. The method further includes flowing gas from within the volume to the environment while at an elevated temperature. The method further includes reducing the temperature to be less than the elevated temperature while preventing gas from flowing from the environment to the volume, thereby creating a pressure within the volume which is less than a pressure outside the volume.

20 Claims, 41 Drawing Sheets

(56) References Cited

U.S. PATENT DOCUMENTS

| | | | |
|---|---|---|---|
| 4,053,362 | A | 10/1977 | Sforza |
| 4,187,861 | A | 2/1980 | Heffernan |
| 4,200,493 | A | 4/1980 | Wilkins et al. |
| 4,280,002 | A | 7/1981 | Bailey et al. |
| 4,282,317 | A | 8/1981 | Roth |
| 4,377,639 | A | 3/1983 | Lee |
| 4,412,626 | A | 11/1983 | Gerhard |
| 4,421,849 | A | 12/1983 | Breuker |
| 4,485,171 | A | 11/1984 | Ikeda et al. |
| 4,492,634 | A | 1/1985 | Villa-Real |
| 4,678,753 | A | 7/1987 | Hempel et al. |
| 4,709,819 | A | 12/1987 | Lattuada et al. |
| 4,851,354 | A | 7/1989 | Winston et al. |
| 4,979,332 | A | 12/1990 | Nagaya et al. |
| 5,005,717 | A | 4/1991 | Oilar |
| 5,026,649 | A | 6/1991 | Lyman et al. |
| 5,122,470 | A | 6/1992 | Banes |
| 5,215,312 | A | 6/1993 | Knappe et al. |
| 5,219,755 | A | 6/1993 | Willemot et al. |
| 5,267,791 | A | 12/1993 | Christian et al. |
| 5,362,642 | A | 11/1994 | Kern |
| 5,376,548 | A | 12/1994 | Matsuo et al. |
| 5,417,576 | A | 5/1995 | Hill |
| 5,449,617 | A | 9/1995 | Falkenberg et al. |
| 5,455,180 | A | 10/1995 | Reid |
| 5,462,874 | A | 10/1995 | Wolf et al. |
| 5,482,711 | A | 1/1996 | Medenica |
| 5,500,369 | A | 3/1996 | Kiplinger |
| 5,693,537 | A | 12/1997 | Wilson et al. |
| 5,695,988 | A | 12/1997 | Chong |
| 5,705,390 | A | 1/1998 | Kadouri et al. |
| 5,763,279 | A | 6/1998 | Schwarz et al. |
| 5,827,681 | A | 10/1998 | Krug et al. |
| 5,842,573 | A | 12/1998 | Halvorsen |
| 5,863,792 | A | 1/1999 | Tyndorf et al. |
| 5,989,913 | A | 11/1999 | Anderson et al. |
| 6,027,938 | A | 2/2000 | Barnes et al. |
| 6,071,088 | A | 6/2000 | Bishop et al. |
| 6,096,562 | A | 8/2000 | Bunn et al. |
| 6,146,875 | A | 11/2000 | Ward |
| 6,156,566 | A | 12/2000 | Bryant |
| 6,204,056 | B1 | 3/2001 | Barnes et al. |
| 6,391,638 | B1 | 5/2002 | Shaaltiel |
| 6,455,310 | B1 | 9/2002 | Barbera-Guillem |
| 6,468,788 | B1 | 10/2002 | Marotzki |
| 6,506,346 | B1 | 1/2003 | Monro |
| 6,666,978 | B2 | 12/2003 | Steinel |
| 6,670,174 | B1 | 12/2003 | Smith et al. |
| 6,855,542 | B2 | 2/2005 | DiMilla et al. |
| 6,869,572 | B1 | 3/2005 | Kopaciewicz et al. |
| 7,358,082 | B2 | 4/2008 | Tsuzuki et al. |
| 7,374,725 | B2 | 5/2008 | Klein et al. |
| 7,428,807 | B2 | 9/2008 | Vander Bush et al. |
| 2002/0106625 | A1 | 8/2002 | Hung et al. |
| 2002/0151044 | A1 | 10/2002 | Lemonnier |
| 2003/0186217 | A1 | 10/2003 | Bader |
| 2004/0005699 | A1 | 1/2004 | Roos et al. |
| 2004/0020889 | A1 | 2/2004 | Willemsen |
| 2004/0029266 | A1 | 2/2004 | Guillem |
| 2005/0084954 | A1 | 4/2005 | Bader |
| 2005/0239197 | A1 | 10/2005 | Katerkamp et al. |
| 2005/0276728 | A1 | 12/2005 | Muller et al. |
| 2006/0141613 | A1 | 6/2006 | Tsuchiya et al. |
| 2006/0172412 | A1 | 8/2006 | Perrie et al. |
| 2006/0275896 | A1 | 12/2006 | Anderson et al. |
| 2006/0281172 | A1 | 12/2006 | Kuwabara et al. |
| 2007/0122869 | A1 | 5/2007 | Hasegawa et al. |
| 2007/0166819 | A1 | 7/2007 | Ghosh |
| 2007/0212747 | A1 | 9/2007 | Browne |
| 2009/0263893 | A1 * | 10/2009 | Cattadoris et al. ......... 435/297.1 |

FOREIGN PATENT DOCUMENTS

| | | | | |
|---|---|---|---|---|
| DE | 19710650 | A1 | | 9/1998 |
| EP | 0 239 697 | | | 10/1986 |
| EP | 0 267 093 | A1 | | 5/1988 |
| EP | 0 380 768 | B1 | | 7/1989 |
| EP | 0 332 753 | A1 | | 9/1989 |
| EP | 0337677 | A2 | * | 10/1989 |
| EP | 0122581 | | | 1/1991 |
| EP | 890636 | A1 | | 1/1999 |
| EP | 0 970 183 | B1 | | 10/2005 |
| FR | 2 639 957 | | | 7/1988 |
| GB | 1134960 | | | 11/1968 |
| GB | 2 263 703 | | | 8/1993 |
| GB | 2302549 | A | | 1/1997 |
| GB | 2305936 | A | | 4/1997 |
| GB | 2361709 | A | | 10/2001 |
| JP | S43-10859 | | | 5/1968 |
| JP | 59/12084 | | | 10/1984 |
| JP | 62-220183 | | | 9/1987 |
| JP | 62-220187 | | | 9/1987 |
| JP | 01/174373 | | | 10/1989 |
| JP | 06343457 | | | 12/1994 |
| JP | 08154663 | | | 6/1996 |
| JP | 2000078963 | | | 3/2000 |
| JP | 2002-513286 | | | 5/2002 |
| JP | 2006-25617 | | | 2/2006 |
| WO | WO 2007/149525 | A2 | | 12/2007 |

OTHER PUBLICATIONS

Goldberg, et al., *Am J. Clin. Path.*, vol. 74, No. 6, 1988, pp. 771-775.
International Search Report for International Publication No. PCT/US2007/07633, completed Jan. 31, 2008, 8 pages.
International Search Report for PCT/US2007/075633, mailed May 15, 2008 in one page.
Millar, et al., *Brit. J. Haematol.*, vol. 69, No. 2, 1988, pp. 197-203.
Office Action for Canadian App. No. 2,660,346 dated Jul. 5, 2010.

* cited by examiner

FIG. 6B
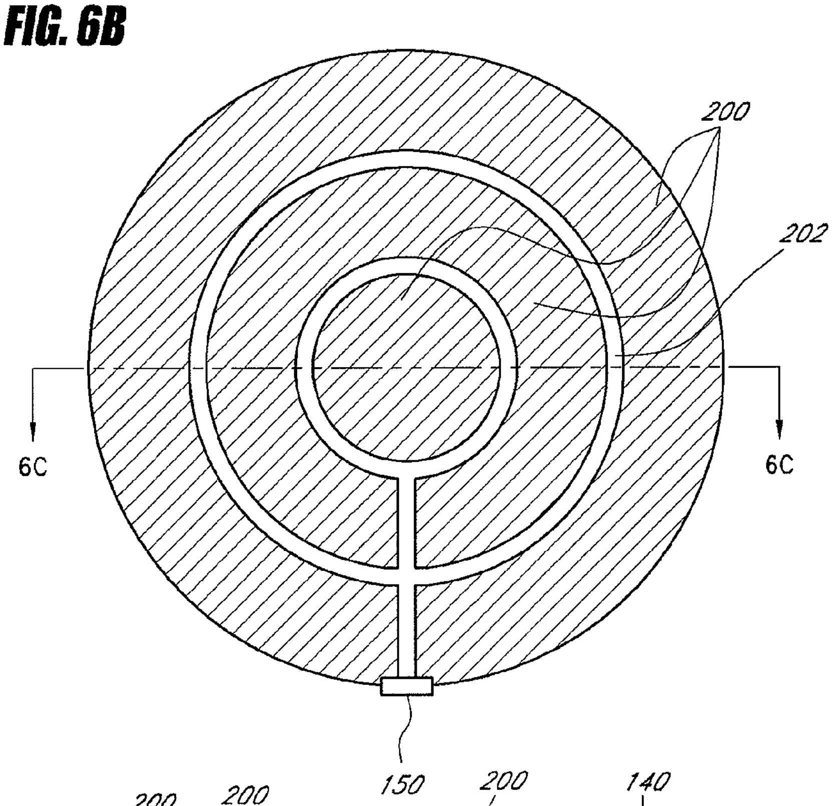
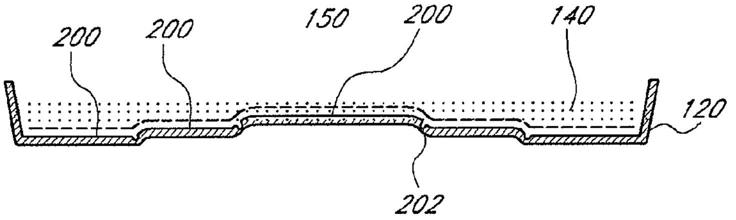
FIG. 6C

METHOD OF PROVIDING PORTABLE BIOLOGICAL TESTING CAPABILITIES

CLAIM OF PRIORITY

This application is a divisional of U.S. patent application Ser. No. 11/836,541, filed on Aug. 9, 2007 and incorporated in its entirety by references herein, which claims the benefit of U.S. Provisional Patent Appl. No. 60/822,004, filed Aug. 10, 2006, which is incorporated in its entirety by reference herein.

BACKGROUND

1. Field of the Invention

The present invention relates generally to biological testing and diagnostic devices and methods.

2. Description of the Related Art

Approximately 6.1 million people, most of them living in tropical, third-world countries, died of preventable, curable diseases in 1998. One of the factors contributing to these deaths is the lack of adequate diagnostic tools in the field. Developing countries do not have the medical resources to provide adequate lab testing and diagnostic procedures to many of their citizens. As a result, treatable disease often goes undiagnosed, leading to death or other serious complications. In addition, diagnostic tools may be unavailable in more developed countries during emergency situations, such as natural disasters, or during wartime.

Standard systems and methods of culturing samples and pathogens using Petri dishes and similar labwear are well known in the fields of microbiology and pathology. In such standard systems, a substrate (e.g., solid or semi-solid agar) is enclosed in an unsealed container designed to vent moisture and to lessen accidental introduction of contaminating microorganisms. A test sample possibly containing unknown microorganisms to be cultured is introduced into the container under sterile conditions. The container is then turned upside-down and placed into an incubator to control temperature, humidity, and other atmospheric conditions, and microorganisms in the test sample are allowed to grow. The upside-down dish/lid combination releases moisture from the dish, so that the moisture does not generally obscure the lid while viewing and moisture drops do not fall onto the surface of agar, contaminating the culture. Thereafter, the container is usually opened to view and confirm the presence of growing microorganisms. Often, this too must be done under sterile conditions because condensation on the lid of the container inhibits viewing, so the lid is removed to view the grown cultures. Various tests can then be applied to the cultured microorganisms in an attempt to identify them, with these tests often taking a significant amount of time. When the identity of a microorganism has been confirmed, this identity often leads to the selection of suitable medical treatment.

SUMMARY

In certain embodiments, a device for providing portable biological testing capabilities free from biological contamination from an environment outside the device is provided. The device comprises a portable housing. The device further comprises a volume surrounded by the housing and sealed against passage of biological materials between the volume and the environment outside the device. The device further comprises a culture medium within the volume. The device further comprises one or more ports configured to provide access to the volume while avoiding biological contamination of the volume. The device further comprises a valve in fluidic communication with the volume and the environment. The valve has an open state in which the valve allows gas to flow from within the volume to the environment outside the device and a closed state in which the valve inhibits gas from flowing between the volume and the environment. The valve switches from the closed state to the open state in response to a pressure within the volume larger than a pressure of the environment outside the device.

In certain embodiments, a method of providing portable biological testing capabilities free from biological contamination from a local environment is provided. The method comprises providing components of a portable device. The components are configured to be assembled together to seal a volume within the device against passage of biological materials between the volume and an environment outside the device. The method further comprises sterilizing the components. The method further comprises providing a sterilized culture medium. The method further comprises assembling the components together with the sterilized culture medium within the volume, thereby forming an assembled device. The method further comprises sterilizing the assembled device, wherein sterilizing the assembled device comprises elevating a temperature of the assembled device. The method further comprises flowing gas from within the volume to the environment while the assembled device is at an elevated temperature. The method further comprises reducing the temperature of the assembled device to be less than the elevated temperature while preventing gas from flowing from the environment to the volume, thereby creating a pressure within the volume which is less than a pressure outside the volume.

In certain embodiments, a method of providing a sterilized volume with a reduced pressure is provided. The method comprises providing a device comprising a volume sealed against passage of biological material between the volume and a region outside the volume; and a valve which can be closed or opened. The valve inhibits gas from flowing from the region to the volume when closed. The valve allows gas to flow from the volume to the region when opened. The valve opens in response to a pressure within the volume being greater than a pressure within the region. The method further comprises sterilizing the volume, wherein said sterilizing increases a temperature within the volume and increases the pressure within the volume to be greater than the pressure within the region. The method further comprises opening the valve in response to the increased pressure within the volume, thereby allowing gas to flow through the valve from the volume to the region. The method further comprises cooling the volume and closing the valve, wherein said cooling decreases the pressure within the volume to create a pressure differential across the valve.

In certain embodiments, a method of using a biological testing device is provided. The method comprises providing a device comprising a housing. The device further comprises a volume surrounded by the housing and sealed against passage of biological materials between the volume and the environment outside the device. The device further comprises a culture medium within the volume. The device further comprises a port configured to provide access to the volume while avoiding biological contamination of the volume. The device further comprises one or more channels within the volume. The one or more channels is in fluidic communication with the port, with the culture medium, and with a region of the volume above the culture medium. The device further comprises a valve in fluidic communication with the volume and the environment. The valve has an open state in which gas flows from within the volume to the environment outside the device and has a closed state in which gas is inhibited from flowing between the volume and the environment. The valve is in the open state in response to a pressure within the volume larger than a pressure of the environment outside the device, thereby reducing the pressure within the volume. The method further comprises elevating a temperature of the volume. The method further comprises opening the valve while the volume is at an elevated temperature. The method further comprises reducing the temperature of the volume while the valve is closed, thereby reducing a pressure within the volume. The method further comprises introducing a liquid specimen to the port at an inlet pressure. The method further comprises flowing the liquid specimen from the port, through the one or more channels, to the culture medium. The flowing of the liquid specimen is facilitated by a pressure differential force between the inlet pressure at the port and the reduced pressure within the volume.

In certain embodiments, a device for providing portable biological testing capabilities free from biological contamination from an environment outside the device is provided. The device comprises a portable housing comprising an inner surface which slopes from a first portion of the housing to a second portion of the housing. The inner surface comprises a plurality of ridges extending along the inner surface from the first portion to the second portion. The device further comprises a volume surrounded by the housing and sealed against passage of biological materials between the volume and the environment outside the device. The device further comprises a culture medium within the volume. The device further comprises one or more ports configured to provide access to the volume while avoiding biological contamination of the volume.

In certain embodiments, a device for providing portable biological testing capabilities free from biological contamination from an environment outside the device is provided. The device comprises a portable housing comprising a substantially optically clear portion. The substantially optically clear portion comprises an outer surface and an inner surface. At least one of the outer surface and the inner surface is curved to form a lens. The device further comprises a volume surrounded by the housing and sealed against passage of biological materials between the volume and the environment outside the device. The device further comprises a culture medium within the volume. The device further comprises one or more ports configured to provide access to the volume while avoiding biological contamination of the volume.

BRIEF DESCRIPTION OF THE DRAWINGS

These and other aspects and advantages of various embodiments will become apparent and more readily appreciated from the following description, taken in conjunction with the accompanying drawings.

FIGS. 6B and 6C schematically illustrate a top view and a cross-sectional view, respectively, of another example configuration of a plurality of segments at the bottom portion of the housing in accordance with certain embodiments described herein.

DETAILED DESCRIPTION

Figure 1:
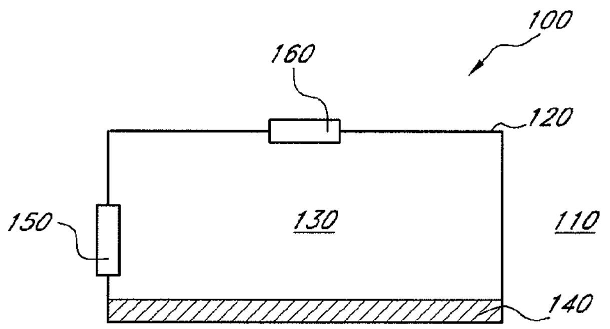
FIG. 1 schematically illustrates an example device in accordance with certain embodiments described herein.

Hereinafter, some embodiments according to the present invention will be described with reference to the accompanying drawings. Here, when one element is connected to another element, one element may be not only directly connected to another element but also indirectly connected to another element via another element. Further, irrelative elements are omitted for clarity. Also, like reference numerals refer to like elements throughout.

Unfortunately, the culture of test samples and simple identifying tests are often out of the reach of third-world medical practices or medical practices in the field. Without an established laboratory, it is often impossible to introduce a test sample into a container without contaminating the culture medium therein. In addition, adequate laboratory equipment (e.g., hoods, microscopes) is often unavailable. Furthermore, it may be impossible to view the cultured microorganisms without compromising sterility, and the lack of experience and instrumentation may preclude even simple tests intended to identify the cultured microorganisms.

A largely unappreciated problem in culturing of unknown microorganisms is that when unexpected organisms are discovered in a culture, the results are frequently dismissed as due to contamination. For example, until fairly recently, it was believed that human blood is essentially sterile except for unusual disease conditions such as sepsis. As a result, when bacteria were recovered from the blood of otherwise healthy patients, the results were ascribed to accidental contamination. It is now known that a small but significant number of bacteria constantly enter the circulatory system (e.g., from the gastrointestinal tract or the gums). This tendency to dismiss culture results as contamination opens our health system to a significant risk. For example, a genetically engineered microorganism (e.g., developed for warfare or terrorism) would look unusual in cultures, and may initially be dismissed as a mere contaminant. Certain embodiments described herein advantageously ensure freedom from contamination to a sufficient extent that unexpected culture results will not be dismissed as being due to contamination.

One object of certain embodiments described herein to provide an inexpensive and portable diagnostic tool by which pathogens can be identified in the field, so appropriate treatment may be administered quickly. For example, certain embodiments described herein provide a mobile medical testing device by which a first responder medical team can test for potential contaminants within a patient's blood. In certain embodiments, the device is advantageous because it allows individuals in the field to identify pathogens and other microorganisms without a lab, a HEPA hood, or other sterile location, and without assistance from a pathologist.

Certain embodiments described herein advantageously provide a method for rapidly isolating infective organisms from a patient and quickly determining which drugs are effective against the isolated organisms, thereby facilitating more rapid and efficacious treatment. The shortened times in providing such diagnostic information using certain embodiments described herein can advantageously save hours or days which would be invaluable in stopping an epidemic. Certain embodiments described herein provide this functionality by maintaining an isolated environment in which pathogens can be cultured and observed. Certain embodiments described herein advantageously keep the cultured pathogens safely sealed during processing, thereby protecting users from exposure.

Under normal circumstances, the natural environment is unfit for the culture and identification of pathogens because there is a high likelihood that the sample will be contaminated by outside microbes and micro-organisms. In addition, many pathogens are "fastidious" and require specialized culture conditions. Preventing contamination of the culture environment is essential; otherwise the diagnostic value of the culture is compromised. Certain embodiments described herein address the problem of contamination by providing an isolated environment in which the environment can be readily modified so that a wide variety of pathogens can be cultured and observed by enclosing culture media in a sealed receptacle. By providing a sealed receptacle, when certain embodiments described herein culture unexpected microbes, the results can be trusted to have come from the patient, thereby allowing diagnosis and evaluation of unusual and/or mutated organisms.

While the sealed receptacle prevents contamination of the cultures grown therein, it creates several potential issues for the maintenance of an environment suitable for culturing pathogens. The interior of the sealed receptacle is a separate environment, sensitive to humidity, temperature, inner and outer pressure, the composition of the biological material under study, and the composition of the culture medium. As a result, certain embodiments described herein incorporate several features to allow manipulation of the interior environment so as to maintain suitable conditions for culture growth.

FIG. 1 schematically illustrates an example device 100 in accordance with certain embodiments described herein. The device 100 can provide portable biological testing capabilities free from biological contamination from an environment 110 outside the device 100. The device 100 comprises a portable housing 120 and a volume 130 surrounded by the housing 120 and sealed against passage of biological materials between the volume 130 and the environment 110 outside the device 100. The device 100 further comprises a culture medium 140 within the volume 130. The device 100 further comprises one or more ports 150 configured to provide access to the volume 130 while avoiding biological contamination of the volume 130. The device 100 further comprises a valve 160 in fluidic communication with the volume 130 and the environment 110. The valve 160 has an open state and a closed state. In the open state, the valve 160 allows gas to flow from within the volume 130 to the environment 110 outside the device 100. In the closed state, the valve 160 inhibits gas from flowing between the volume 130 and the environment 110. The valve 160 switches from the closed state to the open state in response to a pressure within the volume 130 larger than a pressure of the environment 110 outside the device 100.

In certain embodiments, the housing 120 comprises a material that is generally impermeable to biological materials and gases penetrating therethrough. Examples of materials include, but are not limited to, glass, rubber, plastic or thermoplastic. In certain embodiments, the housing 120 is optically clear and comprises polystyrene. The housing 120 is sized to be portable or to be easily transportable. For example, in certain embodiments, the housing 120 is sized to be held in a user's hand. Larger housings 120 can be used in a research laboratory, with the housing 120 having one or more dimensions as large as 24 inches or larger.

Figure 2:
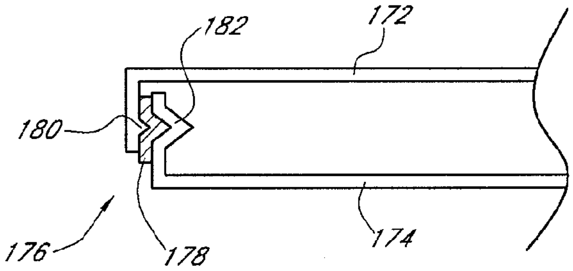
FIG. 2 schematically illustrates a cross-sectional view of an example housing compatible with certain embodiments described herein.

FIG. 2 schematically illustrates a cross-sectional view of an example housing 120 compatible with certain embodiments described herein. The housing 120 in certain embodiments comprises a first portion 172 and a second portion 174. The second portion 174 engages the first portion 172 to form a seal 176 between the first portion 172 and the second portion 174. The seal 176 of certain embodiments comprises wax. In certain embodiments, the first portion 172 comprises a top portion (e.g., lid) of the housing 120 and the second portion 174 comprises a bottom portion (e.g., base) of the housing 120.

In certain embodiments, the housing 120 further comprises one or more sealing members 178 between the first portion 172 and the second portion 174. For example, in certain embodiments, the one or more sealing members 178 comprises a gasket or an O-ring comprising an elastomer material (e.g., medical neoprene, silicone rubber, nylon, plastics). The material for the sealing member 178 is selected in certain embodiments to have little or no outgassing of toxins when gamma radiated, thereby avoiding poisoning of the culture medium 140 within the device 100. The seal 176 between the first portion 172 and the second portion 174 is generally impermeable to biological materials and gases penetrating therethrough. By providing a seal 176 which is generally impermeable to biological materials, the volume 130 within the housing 120 of certain such embodiments described herein is substantially sterile (e.g., substantially free of contamination) and can remain substantially sterile until a user selectively introduces biological material into the volume 130. In certain embodiments, the volume 130 contains air, nitrogen, carbon dioxide, or a noble gas. In certain such embodiments, the volume 130 does not comprise a significant amount of oxygen gas, thereby facilitating anaerobic growth conditions.

In certain embodiments, the first portion 172 comprises one or more protrusions 180 and the second portion 174 comprises one or more recesses 182 configured to engage with the one or more protrusions 180. For example, as schematically illustrated by FIG. 2, the first portion 172 has a "V"-shaped extrusion or protrusion 180 and the second portion 174 has a "V"-shaped indentation or recess 182 that mates with the protrusion 180. Other shapes of the protrusion 180 and the recess 182 (e.g., rounded, rectangular) are also compatible with certain embodiments described herein. In certain embodiments, the sealing member 178 is positioned between the one or more protrusions 180 and the one or more recesses 182. The sealing member 178 is compressed by the one or more protrusions 180 and the one or more recesses 182 to form the seal 176.

In certain embodiments, the first portion 172 and the second portion 174 are generally circular in shape. In certain other embodiments, one or both of the first portion 172 and the second portion 174 can have other shapes (e.g., generally square or generally rectangular) but with structures (e.g., walls, sides, extensions) configured to form a seal with corresponding structures of the other of the first portion 172 and the second portion 174. In certain embodiments, the first portion 172 is rotatable relative to the second portion 174 while maintaining the seal 176 between the first portion 172 and the second portion 174. In certain embodiments, the sealing member 178 comprises a lubricant (e.g., silicone grease) applied to a gasket or O-ring between the first portion 172 and the second portion 174, thereby improving the seal 176 between the first portion 172 and the second portion 174 while facilitating rotation of the first portion 172 relative to the second portion 174. In certain embodiments, the first portion 172 (e.g., a lid) is removably sealed onto the second portion 174 (e.g., a base) with the sealing member 178 (e.g., a gasket) therebetween, thereby forming the seal 176 (e.g., air-tight seal) while allowing rotational movement of the first portion 172 relative to the second portion 174.

Figure 3:
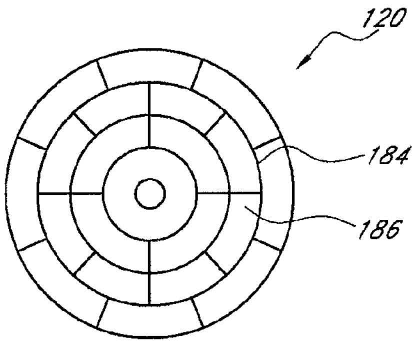
FIG. 3 schematically illustrates a top view of a portion of the housing comprises a plurality of dividers in accordance with certain embodiments described herein.

In certain embodiments, the housing 120 comprises a plurality of dividers 184 in a bottom portion of the housing 120, as schematically illustrated by FIG. 3. The dividers 184 of certain embodiments separate or partition the culture medium 140 placed within the bottom portion of the housing 120 into separate regions 186 which are generally isolated from one another. The separate regions 186 (e.g., compartments or wells) can contain different types of culture media 140 and/or reagents to aid rapid diagnosis. The dividers 184 may extend above the culture medium 140 or the culture medium 140 may be poured or sprayed to be level with the top of the dividers 184. In certain embodiments in which the culture medium 140 is level with the top of the dividers 184, the dividers 184 can be used as a platform for tubes, membranes, screens, or other structures which facilitate diffusion of the liquid specimen across the top surface of the culture medium 140. The different partitioned regions 186 of the culture medium 140 defined by the dividers 184 can then be used to grow multiple, different samples within the device 100 while avoiding cross-contamination of the samples. For example, the bottom portion of the housing 120 can be molded or otherwise equipped with a plurality of ridges in a grid pattern (e.g., circular or rectilinear) that separate the bottom portion of the housing 120 into multiple regions 186 which when containing the culture medium 140, provide substantially independent testing areas for the growth of different organisms. In certain embodiments, the different regions 186 of the culture medium 140 can be accessed by different fluidic channels (e.g., for introducing a liquid specimen), in accordance with certain embodiments described herein. Certain such embodiments advantageously provide the capability to accommodate a plurality of distinct biological samples within a single device 100.

In certain embodiments, the housing 120 can comprise a port covered by a membrane that allows passage of gas into and which is covered by a plastic cover. In certain embodiments, the plastic cover can be removed, allowing gas to pass through the membrane, to facilitate aerobic growth conditions within the volume 130. In certain embodiments, the plastic cover can remain in place, preventing gas from passing through the membrane, to facilitate anaerobic growth conditions within the volume 130.

In certain embodiments, at least a portion of the housing 120 is optically clear, thereby allowing a user to view at least a portion of the volume 130 within the housing 120. The housing 120 of certain embodiments comprises a transparent or optically clear viewing portion 188 (e.g., a window and/or a lens) to facilitate visualization of colonies cultured within the device 100. The viewing portion 188 of certain embodiments comprises polystyrene or another clear plastic material. In certain other embodiments, the viewing portion 188 comprises a sealing film (e.g., Parafilm®, EZ-Pierce™, or ThermalSealRT™ which is available from EXCEL Scientific, Inc. of Wrightwood, Calif.). In certain embodiments, the viewing portion 188 is incorporated in the first portion 172 or in the second portion 174 of the housing 120. In certain embodiments in which the first portion 172 of the housing 120 is rotatable relative to the second portion 174 of the housing 120, the viewing portion 188 is positioned on the first portion 172 away from the axis of rotation such that rotation of the first portion 172 changes the region of the volume 130 (e.g., changes the portion of the cultured colonies) viewable through the viewing portion 188. In certain embodiments, the viewing portion 188 comprises a molded sliding or hinged window on the housing 120 that extends over a moisture collection area of the device 100 (e.g., as shown in FIG. 18B). In certain such embodiments, the viewing portion 188 can be opened (e.g., once the device 100 has been used to culture the pathogens) to provide access to the moisture collection area. In certain embodiments in which it is more convenient to invert the device 100 and view growth taking place through the bottom portion of the housing 120, the bottom portion of the housing 120 can comprise one or more lenses to facilitate or enhance viewing.

Figure 4A:
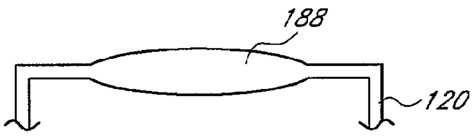
FIGS. 4A and 4B schematically illustrate cross-sectional views of two example viewing portion incorporated into the housing in accordance with certain embodiments described herein.
Figure 4B:
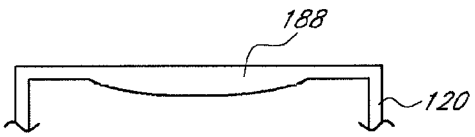

FIGS. 4A and 4B schematically illustrate cross-sectional views of two example viewing portion 188 incorporated into the housing 120 in accordance with certain embodiments described herein. The viewing portion 188 of the housing 120 of FIG. 4A and of FIG. 4B has a varying thicknesses and/or curvatures to form a lens. In FIG. 4A, both the inner surface and the outer surface of the viewing portion 188 are curved to form a convex lens, while in FIG. 4B, only one of the inner surface and the outer surface of the viewing portion 188 is curved to form a plano-convex lens. Other configurations of planar, convex, or concave surfaces can be used for the viewing portion 188 in accordance with certain embodiments described herein. In certain embodiments, the thicknesses and/or curvatures are selected to provide a lens power which places the cultured colonies in sharp focus. The viewing portion 188 of certain embodiments is configured to provide a magnified image (e.g., 1.5× to 2×) of a portion of the culture medium 140. In certain embodiments, a lens of the viewing portion 188 is formed by molding the lens in the same operation that forms the housing 120, while in certain other embodiments, a preformed lens can be attached to a portion of the housing 120.

Figure 5A:
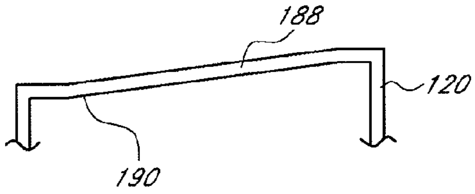
FIGS. 5A and 5B schematically illustrate cross-sectional views of two example viewing portions having a sloped inner surface in accordance with certain embodiments described herein.
Figure 5B:
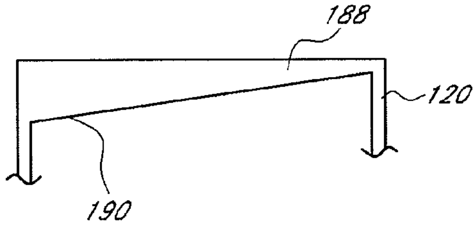

Moisture condensed upon an inner surface 190 of the viewing portion 188 can obstruct or distort the view of the cultured colonies within the volume 130. In certain embodiments, the inner surface 190 of the viewing portion 188 of the housing 120 is sloped (e.g., by 5 to 10 degrees) to facilitate the flow of condensation along the inner surface 190. FIGS. 5A and 5B schematically illustrate cross-sectional views of two example viewing portion 188 having a sloped inner surface 190 in accordance with certain embodiments described herein. The sloped inner surface 190 is configured to direct water droplets condensed onto the inner surface 190 to flow along the inner surface 190, thereby providing a user with a view of the volume 130 substantially unobstructed or affected by moisture on the viewing portion 188.

Figure 5C:
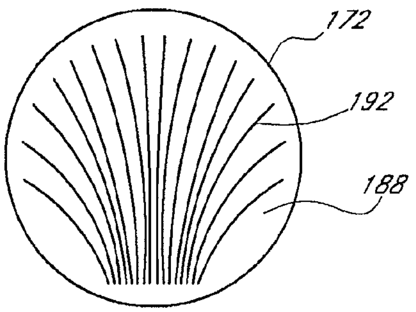
FIG. 5C schematically illustrates a bottom view of a first portion of the housing having a plurality of ridges along at least a portion of the inner surface in accordance with certain embodiments described herein.

In certain embodiments, the inner surface 190 of the viewing portion 188 comprises a plurality of ridges 192 along at least a portion of the inner surface 190. FIG. 5C schematically illustrates a bottom view of a first portion 172 of the housing 120 having a plurality of ridges 192 along at least a portion of the inner surface 190 in accordance with certain embodiments described herein. The plurality of ridges 192 of certain embodiments define a plurality of valleys therebetween which provide locations where water droplets form and would collect, except that they flow away on the ridges 192. The plurality of ridges 192 of certain embodiments in which the inner surface 190 is sloped are continuous and extend along the inner surface 190 in the direction of slope. In certain such embodiments, the ridges 192 can direct droplets of moisture that would otherwise accumulate and provide paths for condensation flow, thereby facilitating the flow of moisture condensed onto the inner surface 190 of the viewing portion 188 to a predetermined area (e.g., a collection site or liquid-retaining region or a predetermined portion of the culture medium 140 surface) within the volume 130 where the moisture is received. In certain such embodiments, the area is accessible through at least one of the ports 150 or through a sliding or hinged window of the viewing portion 188 (e.g., as shown in FIG. 18B) such that a sample of the collected moisture can be removed from the volume 130 through the port 150 for analysis.

The culture medium 140 of certain embodiments is configured to facilitate the growth and multiplication of cells or pathogens in a liquid specimen (e.g., containing blood, blood components, pus, urine, mucus, feces, microbes obtained by throat swab, sputum, or cerebrospinal fluid introduced to the culture medium 140. In certain embodiments, the culture medium 140 comprises a agar composition fortified with nutrients for optimum growth, but can be any of a number of solid or semi-solid culture materials gelled with agar or gelatin or the like. In certain embodiments, the culture medium 140 is liquid when heated and is poured or sprayed into the volume 130 under sterile conditions and is allowed to cool and to solidify. In certain embodiments, the culture medium 140 at least partially fills a bottom portion of the housing 120 and is in contact with an inner surface of the bottom portion of the housing 120. In certain embodiments, a releasing agent may be added or applied to the culture medium 140. In certain embodiments, the culture medium 140 is in liquid form.

In certain embodiments, the culture medium 140 has an upper surface where cells or pathogens can be introduced and allowed to grow and multiply. In certain other embodiments, the device 100 comprises one or more thin, hollow regions adjacent to the culture medium 140. These regions are configured to receive a liquid specimen containing cells or pathogens to be cultured within the device 100. In certain embodiments, the culture medium 140 is spaced from an inner surface of the bottom portion of the housing 120, thereby defining one or more thin hollow regions therebetween. In certain embodiments, the culture medium 140 comprises two or more portions (e.g., two or more layers) having one or more thin hollow regions (e.g., one or more discontinuities or cracks) therebetween. Thus, in certain embodiments in which the regions between the portions of the culture medium 140 are not significantly exposed to the atmosphere within the volume 130, a first, in vivo sample can grow in the discontinuity or between the layers of the culture medium 140 anaerobically while a second sample can grow aerobically on the upper surface of the culture medium 140. Colonies grown in these regions between the portions of the culture medium 140 in certain embodiments are readily observable through the culture medium 140.

U.S. Pat. No. 6,204,056, which is incorporated in its entirety by reference herein, discloses various embodiments in which a discontinuity between portions of the culture medium 140 is maintained to receive a liquid specimen and to provide a specialized environment that allows culture of cells, organisms, or anaerobes that will not normally grow on the upper surface of the culture medium 140. For example, in certain embodiments, the culture medium 140 comprises a first layer and a second layer having one or more generally flat and thin hollow regions therebetween. In certain embodiments, these regions comprise one or more elongate conduits (e.g., tubes) having a plurality of orifices (e.g., holes or slits) along the length of the one or more conduits and in fluidic communication with the one or more generally flat and thin regions, thereby providing a flowpath through which a liquid specimen can flow to the culture medium 140. In certain other embodiments, the device 100 comprises one or more porous or semi-permeable layers (e.g., membranes, meshes, nettings, or screens) between and physically separating the first and second layers of the culture medium 140 to form the region. The liquid specimen introduced to the region between the first and second layers is able to access one or both of the first and second layers.

Figure 6A:
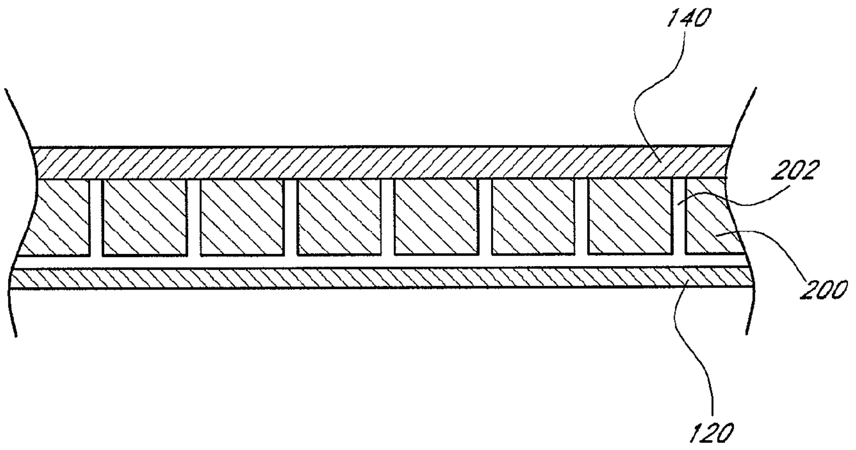
FIG. 6A schematically illustrates a cross-sectional view of an example configuration of a plurality of segments at the bottom portion of the housing in accordance with certain embodiments described herein.

FIG. 6A schematically illustrates a cross-sectional view of an example configuration of a plurality of segments 200 at the bottom portion of the housing 120 in accordance with certain embodiments described herein. The bottom portion of the housing 120 comprises a plurality of segments 200 having a plurality of channels 202 therebetween. As shown in FIG. 6, in certain embodiments, the channels 202 are formed by the sides of the segments 200. In certain embodiments, the top surfaces of the plurality of segments 200 are generally flat, such that the segments 200 are plateau-like. The plurality of channels 202 is configured to allow a liquid specimen or reagent to flow therethrough, and at least a portion of the plurality of channels 202 is adjacent to the culture medium 140.

FIGS. 6B and 6C schematically illustrate a top view and a cross-sectional view, respectively, of another example configuration of a plurality of segments 200 at the bottom portion of the housing 120 in accordance with certain embodiments described herein. The segments 200 of FIGS. 6B and 6C are plateaus with the culture medium 140 poured or sprayed thereon. The channels 202 extend along the periphery of the plateaus as shown in FIG. 6B.

Figure 7A:
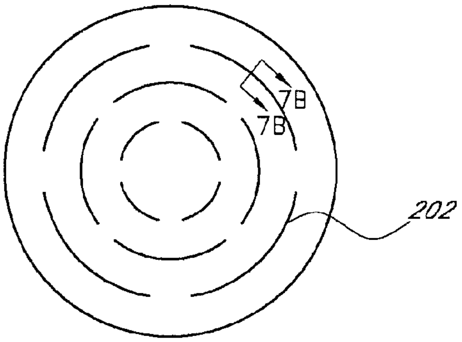
FIGS. 7A and 7B schematically illustrate a top view and cross-sectional view, respectively, of an example pattern of the plurality of channels in accordance with certain embodiments described herein.
Figure 7B:

FIGS. 7A and 7B schematically illustrate a top view and cross sectional view of an example pattern of the plurality of channels 202 extending through at least a portion of the culture medium 140 in accordance with certain embodiments described herein. The pattern of FIG. 7A is a grid pattern or a "maze" pattern substantially evenly distributed across the culture medium 140. Various other patterns of the plurality of channels 202 in which the channels 202 provide rapid and even distribution of the liquid specimen or reagent through the channels 202 are also compatible with various embodiments described herein.

Figure 8:
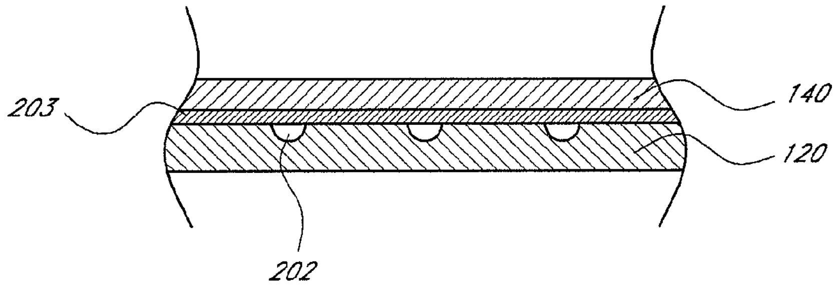
FIG. 8 schematically illustrates a cross-sectional view of a plurality of channels and a semi-permeable layer beneath the culture medium in accordance with certain embodiments described herein.

As shown in FIG. 6A, the culture medium 140 covers at least a portion of the plurality of channels 202 but does not significantly fill the plurality of channels 202. For example, when in its liquid form, the culture medium 140 of certain embodiments has a sufficiently high surface tension that it does not fill the relatively narrow channels 202 while being poured into the volume 130. In certain other embodiments, a semi-permeable layer 203 (e.g., membrane such as dialysis membrane, nylon mesh, netting, or screen) is between the culture medium 140 and the plurality of channels 202. For example, as schematically illustrated by FIG. 8, a plurality of channels 202 formed in the bottom surface of the housing 120 are covered by a semi-permeable layer 203 with the culture medium 140 over the semi-permeable layer 203. The semi-permeable layer 203 allows at least a portion of the liquid specimen (e.g., small molecules) within the plurality of channels 202 to cross the semi-permeable layer 203 and access the culture medium 140. In certain embodiments, the semi-permeable layer 203 comprises a plurality of punctures (e.g., by a needle or a micro-laser beam) at predetermined locations in fluidic communication with the plurality of channels 202 to allow the liquid specimen to readily penetrate the semi-permeable layer 203.

In certain embodiments, the segments 200 are integral portions of the housing 120 (e.g., extruded portions of the bottom portion of the housing 120). The bottom portion of the housing 120 can be etched, embossed, or otherwise machined to form the plurality of channels 202 in certain embodiments. In certain other embodiments, the segments 200 are portions of a member (e.g., a generally flat plate or layer) which is placed in the bottom portion of the housing 120 and which can be adhered to the bottom portion of the housing 120 prior to pouring the culture medium 140 over the member. In certain embodiments, the member can be placed over a first layer of the culture medium 140 and additional culture medium 140 can be poured over the member, thereby creating two layers of culture medium 140 with a discontinuity therebetween. In certain such embodiments, a region between the member and the bottom portion of the housing 120 can provide a conduit for fluid flow. The member of certain embodiments comprises a generally inert material (e.g., glass, ceramic, plastic) which does not significantly react with the other materials placed within the volume 130. The member can be etched, embossed, or otherwise machined to form the plurality of channels 202 in certain embodiments.

Figure 9:
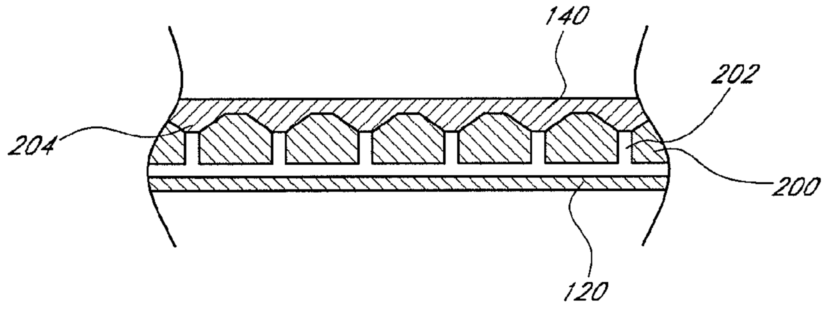
FIG. 9 schematically illustrates a cross-sectional view of another example configuration of a plurality of segments at the bottom portion of the housing in accordance with certain embodiments described herein.

FIG. 9 schematically illustrates a cross-sectional view of another example configuration of a plurality of segments 200 at the bottom portion of the housing 120 in accordance with certain embodiments described herein. The segments 200 have beveled portions such that the channels 202 formed by the beveled portions have a funnel-shaped or infundibuliform portion 204, as shown in the cross-sectional view of FIG. 9. In certain embodiments, the infundibuliform portions 204 can be generally circular, generally square, generally rectangular, or any other shape in a plane generally perpendicular to the cross-sectional plane of FIG. 9. As shown in FIG. 9, the culture medium 140 covers the plurality of channels 202 and fills the top portions of the infundibuliform portions 204, but does not significantly fill the underlying portions of the plurality of channels 202. In certain embodiments, each infundibuliform portion 204 comprises a semi-permeable layer (e.g., membrane, nylon mesh, netting, or screen) between the culture medium 140 and the underlying portion of the plurality of channels 202, the semi-permeable layer allowing the liquid specimen within the underlying portion of the plurality of channels 202 to access the culture medium 140.

Figure 10:
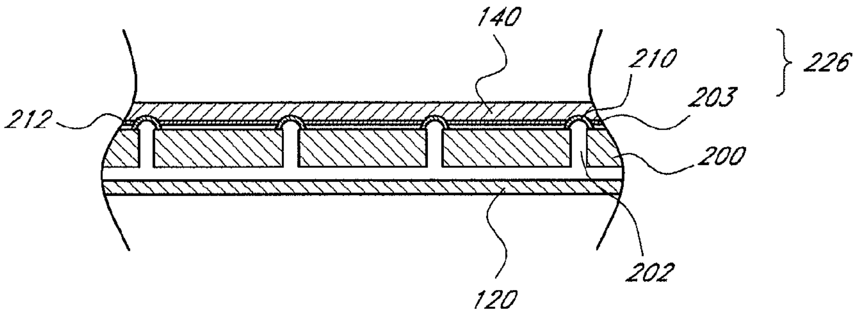
FIG. 10 schematically illustrates a cross-sectional view of another example configuration of a plurality of segments at the bottom portion of the housing in accordance with certain embodiments described herein.

FIG. 10 schematically illustrates a cross-sectional view of another example configuration of a plurality of segments 200 at the bottom portion of the housing 120 in accordance with certain embodiments described herein. An assembly 226 comprising a semi-permeable layer 203 and a plurality of elongate conduits 210 is positioned within the volume 130 and over the plurality of segments 200. The plurality of conduits 210 overlays the plurality of channels 202 formed by the sides of the segments 200, and the conduits 210 are in fluidic communication with the plurality of channels 202. The semi-permeable layer 203 is spaced away from the top surface of the plurality of segments 200, thereby forming a thin, hollow region 212 therebetween. The plurality of conduits 210 in certain embodiments comprises a plurality of tubular portions with a plurality of orifices (e.g., holes or slits) along the sides of the tubular portions and configured to allow a liquid specimen or reagent introduced into the plurality of channels 202 to flow through the tubular portions and into the thin, hollow region 212 between the plurality of segments 200 and the culture medium 140. While each conduit 210 of FIG. 10 has a generally semi-circular cross-section, other cross-sectional shapes (e.g., generally rectangular) are also compatible with certain embodiments described herein.

Figure 11A:
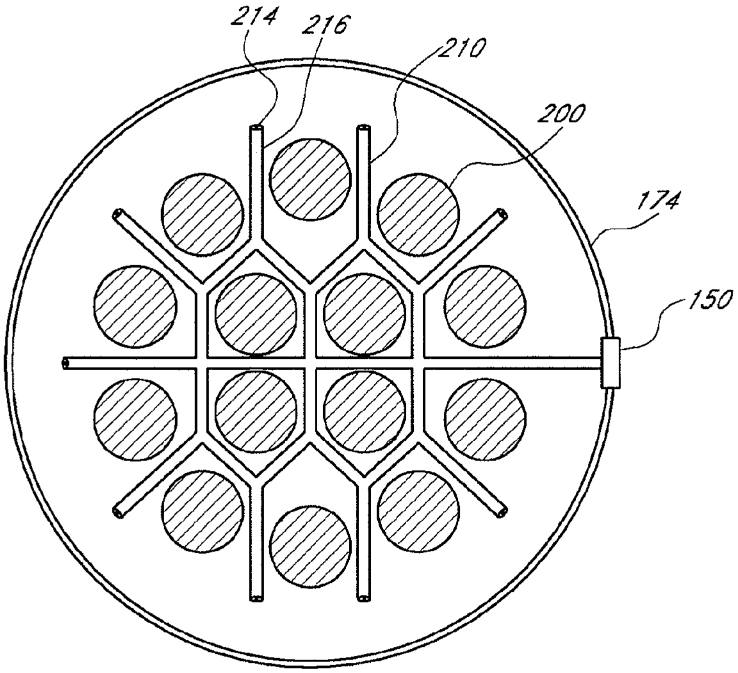
FIG. 11A schematically illustrates a top view of an example configuration of a plurality of segments in accordance with certain embodiments described herein.

FIG. 11A schematically illustrates a top view of an example configuration of a plurality of segments 200 in accordance with certain embodiments described herein. The segments 200 schematically illustrated have a generally circular shape, but other shapes (e.g., generally hexagonal, generally square, generally rectangular, irregularly-shaped) are also compatible with certain embodiments described herein. The segments 200 of certain such embodiments are elevated extrusions or plateaus extending from the bottom portion of the housing 120. The segments 200 are spaced from one another and the region between the segments 200 contains a plurality of elongate conduits 210 in fluidic communication with a port 150 through which a liquid specimen can be introduced into the conduits 210 and around each segment 200. The conduits 210 comprises a plurality of orifices (e.g., holes or slits) through which the liquid specimen can access the culture medium 140. The conduits 210 have one or more orifices 214 in one or more ends 216 of the conduits 210, the orifices 214 in fluid communication with the port 150 via the conduits 210. In certain embodiments, the majority of the conduits 210 are within the culture medium 140, but the ends 216 extend above the culture medium 140 such that the orifices 214 are in fluidic communication with the region of the volume 130 above the culture medium 140.

In certain embodiments in which the volume 130 has a reduced pressure as compared to the region outside the device 100, a pressure differential between the port 150 and the orifices 214 advantageously facilitates flow of the liquid specimen or reagent through the plurality of conduits 210. In certain such embodiments, the orifices 214 are sized such that the liquid specimen does not flow out of the orifices 214. Instead, the orifices 214 are blocked by the liquid specimen. In this way, certain embodiments described herein advantageously maintain a pressure differential between the port 150 and each unblocked orifice 214 to provide a pressure differential force which facilitates flow of the liquid specimen into the conduit 210 in a direction of the unblocked orifice 214.

Figure 11B:
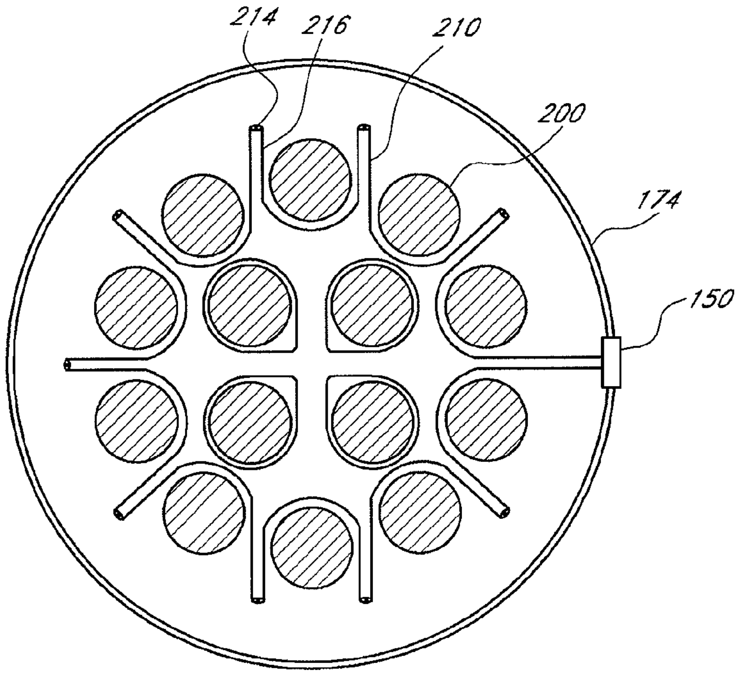
FIG. 11B schematically illustrates a top view of another example configuration of a plurality of segments with a plurality of conduits between the segments in accordance with certain embodiments described herein.
Figure 11C:
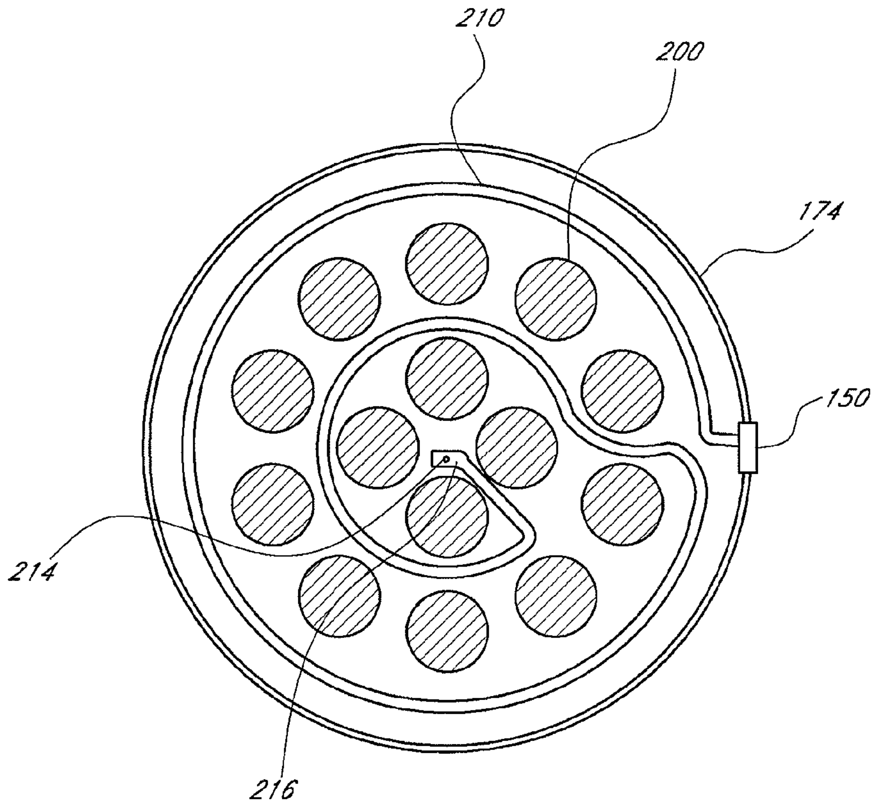
FIG. 11C schematically illustrates a top view of another example configuration of a plurality of segments with a single conduit between the segments in accordance with certain embodiments described herein.

FIG. 11B schematically illustrates a top view of another example configuration of a plurality of segments 200 with a plurality of conduits 210 between the segments 200 in accordance with certain embodiments described herein. The conduits 210 schematically illustrated by FIG. 11B comprise a pair of flat membranes (e.g., semi-permeable membranes), one on top of the other, to form the conduits 210 therebetween. In certain embodiments, the two membranes are bonded together at various positions along their edges. FIG. 11C schematically illustrates a top view of another example configuration of a plurality of segments 200 with a single conduit 210 between the segments 200 in accordance with certain embodiments described herein. The conduit 210 is positioned along and between the segments 200 (e.g., in a serpentine configuration). The conduit 210 has an end 216 which extends above the culture medium 140 with an orifice 214 in fluidic communication with the port 150 and the volume 130. Other configurations of the conduits 210 are also compatible with certain embodiments described herein.

Figure 12A:
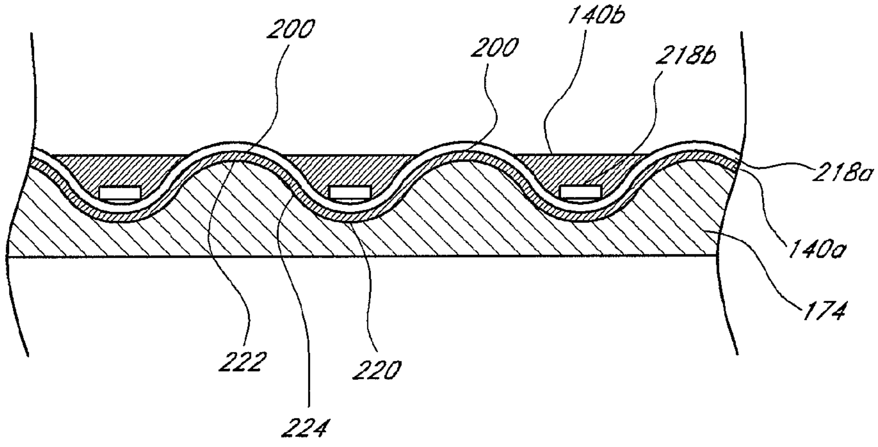
FIG. 12A schematically illustrates a cross-sectional view of an example configuration of a plurality of segments with a plurality of conduits therebetween.

FIG. 12A schematically illustrates a cross-sectional view of an example configuration of a plurality of segments 200 with a plurality of conduits 210 therebetween. The segments 200 are spaced from one another and have the conduits 210 positioned between the segments 200. In certain embodiments, the conduits 210 comprise elongate tubes having a plurality of orifices along their length, while in certain other embodiments, the conduits 210 comprise two semi-permeable layers 218*a*, 218*b* (e.g., a membrane, screen, or fabric comprising nylon or polyester) formed together to provide a flowpath for the liquid specimen. To form the configuration schematically illustrated by FIG. 12A, a first layer 140*a* of the culture medium 140 is deposited (e.g., sprayed or poured) onto the second portion 174 of the housing 120, with the first layer 140*a* covering the segments 200 and the regions between the segments 200. A first semi-permeable layer 218*a* is placed over the first layer 140*a* of the culture medium 140 so as to cover the segments 200 and the regions between the segments 200. A second semi-permeable layer 218*b* is placed over the first semi-permeable layer 218*a* in the regions between the segments 200. A second layer 140*b* of the culture medium 140 is deposited (e.g., sprayed or poured) into the regions between the segments 200, thereby covering the first semi-permeable layer 218*a* and the second semi-permeable layer 218*b*. In certain such embodiments, the region between the first semi-permeable layer 218*a* and the second semi-permeable layer 218*b* serves as a conduit 210 through which the liquid specimen can flow and can access the culture medium 140. In certain such embodiments, the liquid specimen can be rapidly distributed throughout the culture medium 140 around each segment 200, facilitated at least in part by a pressure differential force between the volume 130 and the port 150 through which the liquid specimen is introduced to the volume 130.

Certain such embodiments advantageously provide three different types of regions in which pathogens may grow. A first region 220 in or near the first layer 140*a* of the culture medium 140 is a hospitable location for anaerobic pathogens to grow since this first region 220 is substantially isolated from the atmosphere above the culture medium 140. A second region 222 on top of the second layer 140*b* of the culture medium 140 is a hospitable location for aerobic pathogens to grow since this second region 222 is in fluidic communication with the atmosphere above the culture medium 140. A third region 224 along the sloping sides of the segments 200 is a hospitable location for aerophilic pathogens to grow since this third region 224 has a varying concentration of oxygen from the lower portion to the upper portion of the segment 200. Certain such embodiments advantageously provide more surface area for culture growth.

Figure 12B:
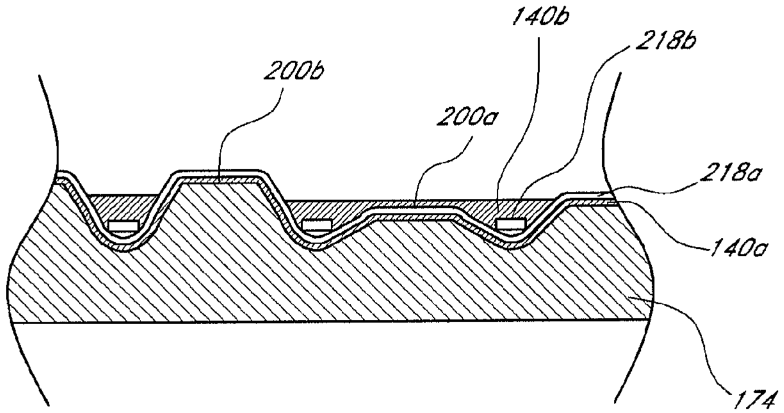
FIG. 12B schematically illustrates a cross-sectional view of another example configuration of a plurality of segments with a plurality of conduits therebetween.

FIG. 12B schematically illustrates a cross-sectional view of another example configuration of a plurality of segments 200 with a plurality of conduits 210 therebetween. The segments 200 comprise a first set of segments 200*a* having a first height and a second set of segments 200*b* having a second height higher than the first height. The second layer 140*b* of the culture medium 140 substantially covers the first set of segments 200*a* but does not cover the second plurality of segments 200*b*.

Figure 12C:
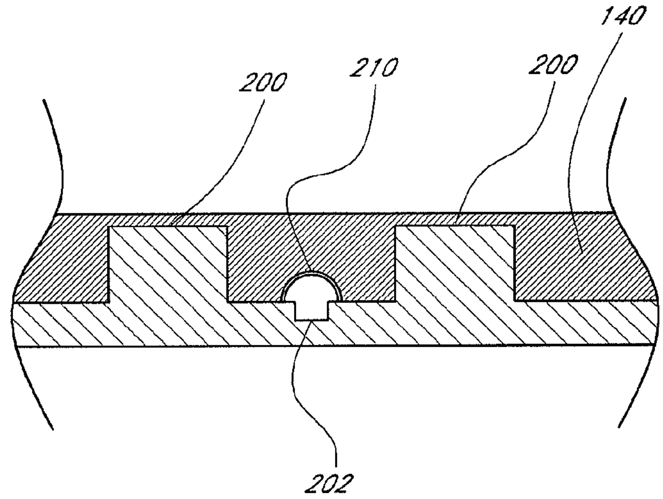
FIG. 12C schematically illustrates a cross-sectional view of another example configuration of a plurality of segments with a plurality of conduits therebetween.

FIG. 12C schematically illustrates a cross-sectional view of another example configuration of a plurality of segments 200 with a plurality of conduits 210 therebetween. The conduits 210 schematically illustrated by FIG. 12C have a generally semi-circular cross-section, although other cross-sectional shapes (e.g., generally circular, generally oval, generally hexagonal, or generally rectangular) are also compatible with certain embodiments described herein. The conduits 210 are positioned in the regions between the segments 200. While FIG. 12C shows a channel 202 below the conduit 210, other embodiments do not have this channel 202. The culture medium 140 covers the conduits 210 and the segments 200. The conduits 210 have a plurality of orifices along their lengths to allow the liquid specimen to access the culture medium 140.

Figure 12D:
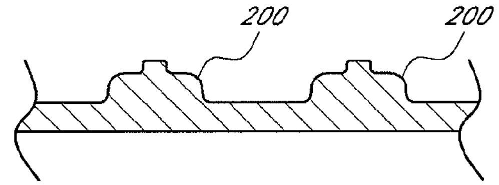
FIG. 12D schematically illustrates a cross-sectional view of another example configuration of a plurality of segments in accordance with certain embodiments described herein.

FIG. 12D schematically illustrates a cross-sectional view of another example configuration of a plurality of segments 200 in accordance with certain embodiments described herein. Each of the segments 200 has two or more plateaus, which can be flat or curved. The culture medium 140 can be sprayed or poured into the volume 130 and a membrane or screen having channels affixed thereto can be inserted over the culture medium 140. In certain embodiments, the membrane or screen has holes configured to be placed over the topmost plateau of the segments 200 shown in FIG. 12D, such that the topmost plateau is not covered by the membrane or screen. In certain such embodiments, as described above with regard to FIGS. 12A and 12B, the plateaus provide regions which have differing exposure to the atmosphere within the volume 130. These differing regions (e.g., deep below the top surface of the culture medium 140, just barely beneath the top surface of the culture medium 140, and on the top surface of the culture medium 140) can be used to diagnose the aerobic, anaerobic, or microaerophilic nature of the pathogens grown within the volume 130.

Figure 13A:
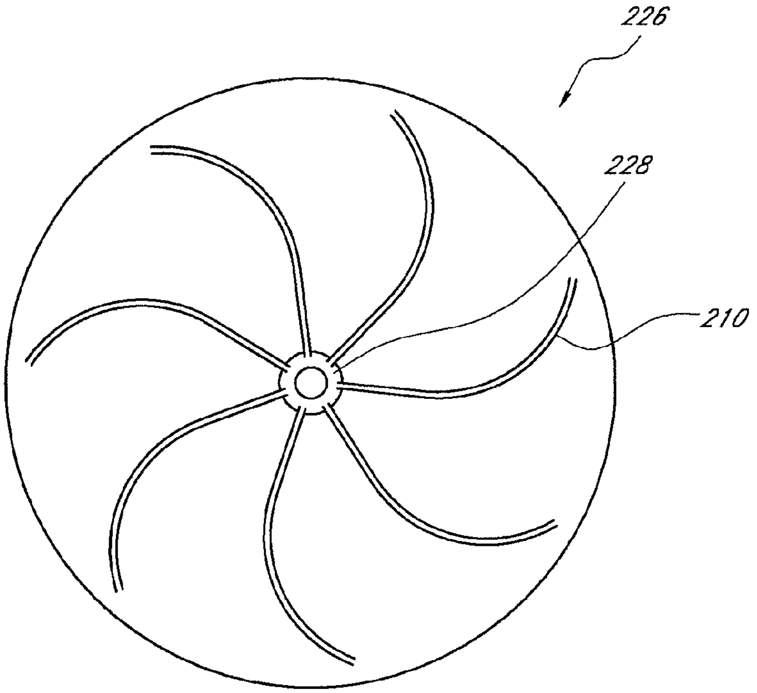
FIGS. 13A and 13B schematically illustrate top views of two example members having a plurality of elongate conduits in accordance with certain embodiments described herein.
Figure 13B:
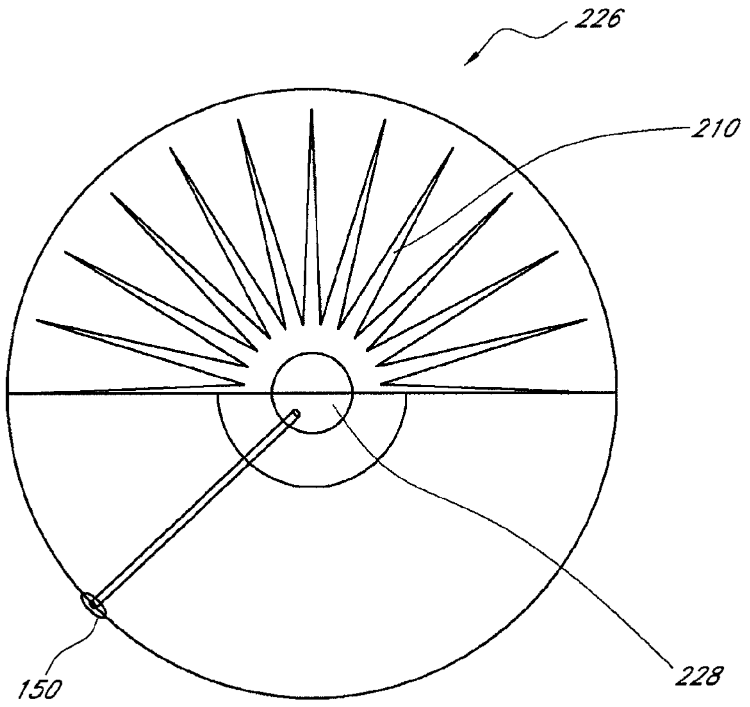

FIGS. 13A and 13B schematically illustrate top views of two example members 226 in accordance with certain embodiments described herein. The member 226 of FIG. 13A comprises a plurality of elongate conduits 210 (e.g., tubular portions) with a plurality of orifices (e.g., holes or slits)(not shown) along the sides of the conduits 210. The member 226 of FIG. 13B comprises a plurality of elongate conduits 210 having cross sections which are more narrow in the periphery of the device 100 as compared to the center of the device 100. In certain embodiments, the member 226 further comprises an access portion 228 in fluidic communication with the plurality of conduits 210. In certain such embodiments, the access portion 228 is configured to provide a single fluidic access to the plurality of conduits 210 such that a liquid specimen introduced to the access portion 228 flows through the plurality of conduits 210 to be distributed along the culture medium 140. In certain embodiments, as schematically illustrated by FIG. 13, the access portion 228 is centrally located and the plurality of conduits 210 is in a general spiral-like configuration. Other positions of the access portion 228 and other configurations of the plurality of conduits 210 (e.g., substantially straight, extending radially from a central position, rectilinear) are also compatible with certain embodiments described herein. In certain embodiments, the member 226 can be positioned on a first layer of the culture medium 140 previously placed within the volume 130, and a second layer of the culture medium 140 can be placed over the plurality of conduits 210. In this way, the member 226 provides fluidic access to an interstitial region between the first layer and the second layer of the culture medium 140. In certain embodiments, the member 226 further comprises a semi-permeable layer 203 which separates the first layer of the culture medium 140 from the second layer of the culture medium 140.

Figure 14A:
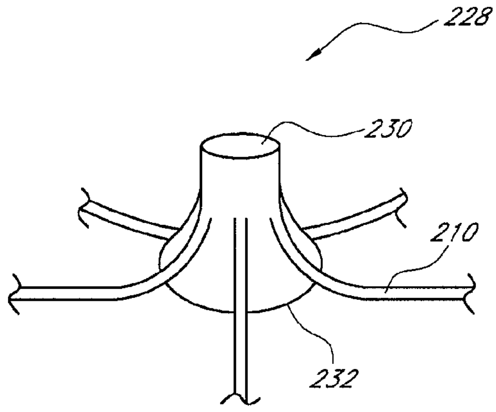
FIGS. 14A and 14B schematically illustrate perspective views of two example access portions in accordance with certain embodiments described herein.
Figure 14B:
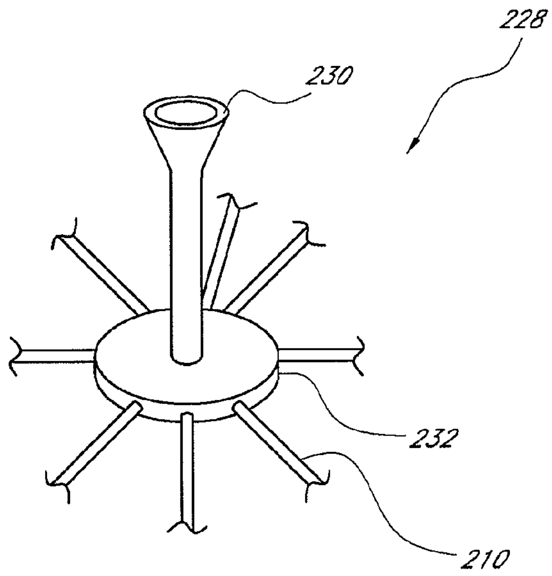

FIGS. 14A and 14B schematically illustrate perspective views of two example access portions 228 in accordance with certain embodiments described herein. The access portion 228 shown in FIG. 14A is in fluidic communication with the plurality of conduits 210 and comprises an injection port 230 configured to receive a syringe needle. In certain embodiments, the access portion 228 comprises an expandable portion 232 configured to expand to receive an amount of the liquid specimen (e.g., from a syringe needle) and to contract to provide a force which facilitates flow of the liquid specimen through the conduits 210. In certain such embodiments, the access portion 228 comprises an elastomer material which is puncturable by a syringe needle, self-sealing after the syringe needle is removed, and which can expand and contract in accordance with certain embodiments described herein. The access portion 228 shown in FIG. 14B comprises an injection port 230 configured to receive a syringe needle and which extends towards a port 150 on the first portion 172 of the housing 120.

Figure 14C:
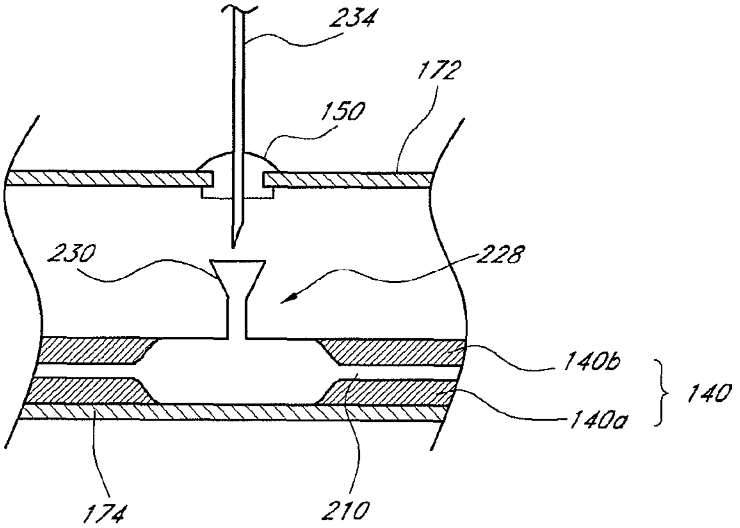
FIG. 14C schematically illustrates a cross-sectional view of another example access portion in accordance with certain embodiments described herein.

FIG. 14C schematically illustrates a cross-sectional view of another example access portion 228 in accordance with certain embodiments described herein. The access portion 228 of FIG. 14C is positioned on the second portion 174 of the housing 120 and is surrounded by a first layer 140*a* of the culture medium 140 and a second layer 140*b* of the culture medium 140. The plurality of conduits 210 are in fluidic communication with the region between the first layer 140*a* and the second layer 140*b* of the culture medium 140. As shown in FIGS. 14B and 14C, in certain embodiments, the injection port 230 is below a port 150 on the first portion 172 of the housing 120 such that a syringe needle 234 extending through the port 150 can be inserted in to the injection port 230. In certain embodiments, the injection port 230 is configured to mate with the needle 234 such that an air-tight seal is formed. Certain such embodiments allow a pressure differential to exist between the region within the injection port 230 and the region outside the injection port 230.

Figure 14D:
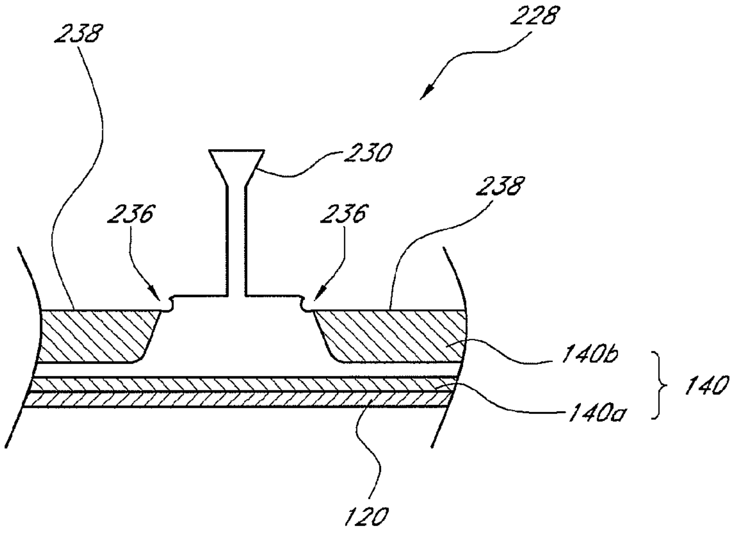
FIG. 14D schematically illustrates a cross-sectional view of another example access portion in accordance with certain embodiments described herein.

FIG. 14D schematically illustrates a cross-sectional view of another example access portion 228 in accordance with certain embodiments described herein. The access portion 228 of FIG. 14D has a plurality of openings 236 positioned to allow a portion of the liquid specimen placed into the access portion 228 to flow to a top surface 238 of the culture medium 140. Various configurations of the openings 236 are compatible with certain embodiments described herein. In certain embodiments, the openings 236 are initially closed and below the top surface of the culture medium 140. When the liquid specimen is introduced into the access portion 228, the access portion 228 expands such that the openings 236 move to a position at or above the top surface of the culture medium 140 and open so that the liquid specimen (e.g., a few drops) can flow therethrough to the top surface of the culture medium 140. When a sufficient amount of the liquid specimen has flowed out of the access portion 228 (either through the openings 228 or through the conduits 210), the access portion 228 shrinks such that the openings 236 return to below the top surface of the culture medium 140 and are closed. Certain such embodiments advantageously provide an easy procedure for a user to introduce the liquid specimen to both the top surface of the culture medium 140 and the conduits 210 in a single action.

Figure 15:
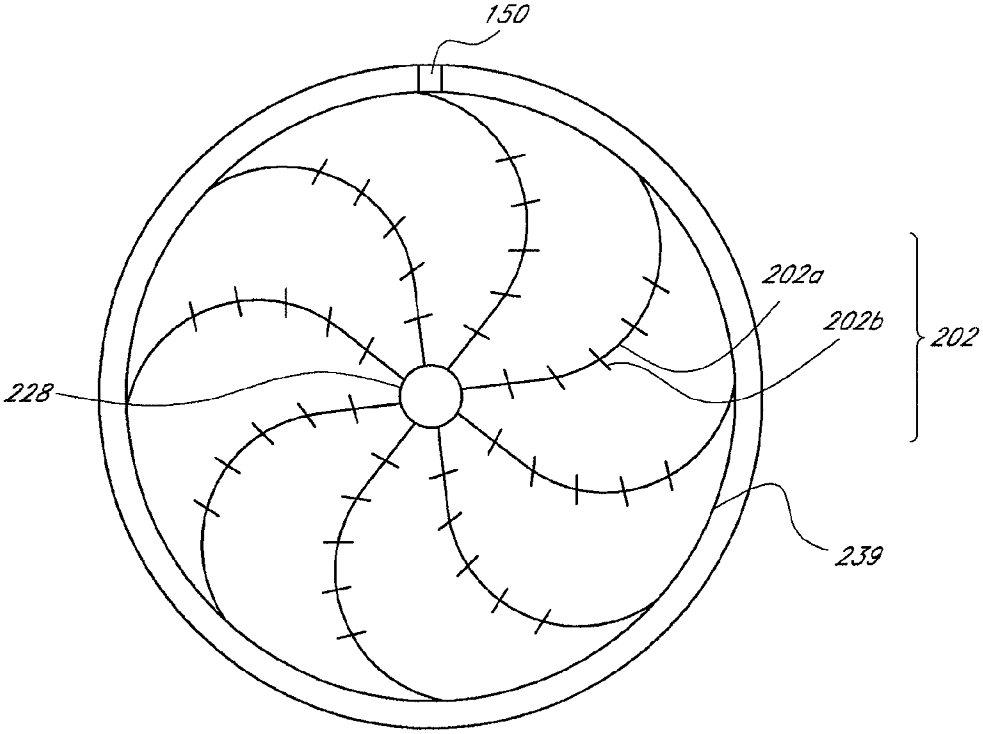
FIG. 15 schematically illustrates a top view of an example configuration of the channels in accordance with certain embodiments described herein.

FIG. 15 schematically illustrates a top view of an example configuration of the channels 202 in accordance with certain embodiments described herein. For example, in certain embodiments, the plurality of channels 202 comprises a plurality of spiral-shaped main channels 202*a*, with each main channel 202*a* in fluidic communication with a plurality of side channels 202*b* extending generally away from each main channel 202*a*. In certain embodiments, the side channels 202*b* are open on one end and are spaced along each main channel 202*a* to allow liquid specimen to diffuse into the culture medium 140 away from the main channel 202*a*. Each main channel 202*a* is in fluidic communication with the access portion 228 configured to provide a single fluidic access to the plurality of channels 202.

The liquid specimen or reagent in certain embodiments flows through the plurality of channels 202 by capillary action. In certain embodiments, the channels 202 are in fluidic communication with a region configured to have suction applied thereto. The suction and the capillary action draw the liquid specimen or reagent through the channels 202.

For example, in certain embodiments, each main channel 202*a* is also in fluidic communication with a generally circular channel 239 located near the periphery of the housing 120, as schematically illustrated in FIG. 15. The channel 239 of certain embodiments is configured to have suction applied thereto, thereby creating a pressure differential between the access portion 228 and the channel 239. For example, in certain embodiments, the channel 239 is in fluidic communication with a port 150 configured to be in fluidic communication with a vacuum-containing tube (e.g., Vacutainer® available from Becton, Dickinson & Co. of Franklin Lakes, N.J.). This pressure differential between the access portion 228 and the channel 239 can facilitate the flow of the liquid specimen from the access portion 228 through the main channels 202*a* and the side channels 202*b*.

Figure 16:
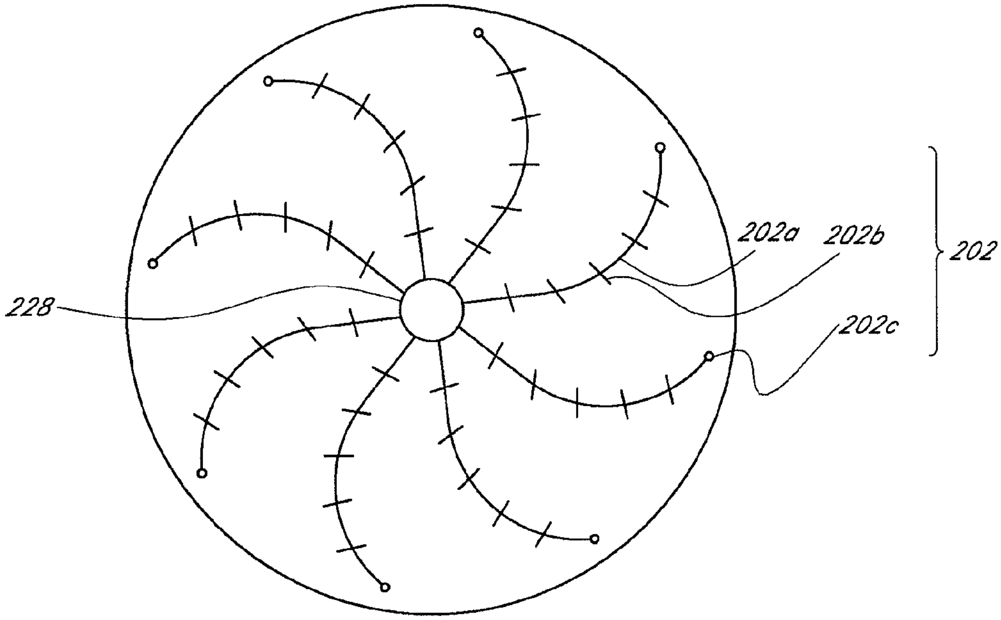
FIG. 16 schematically illustrates a top view of another example configuration of the channels in accordance with certain embodiments described herein.

FIG. 16 schematically illustrates a top view of another example configuration of the channels 202 in accordance with certain embodiments described herein. The plurality of channels 202 comprises a plurality of upward channels 202*c* which, in certain embodiments, extends through at least a portion of the culture medium 140 and is in fluidic communication with the main channels 202*a* and with a region of the volume 130 above the culture medium 140. When the region above the culture medium 140 is at a reduced pressure (e.g., suction is applied to the volume 130), the liquid specimen can be drawn through the plurality of channels 202 by the pressure differential between one portion of the channels 202 (e.g., the access portion 228) and the region of the volume 130 above the culture medium 140.

Figure 17A:
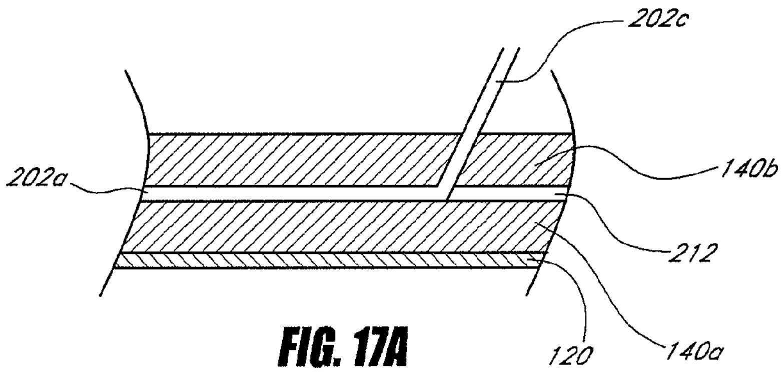
FIGS. 17A-17C schematically illustrate cross-sectional views of example main channels and upward channels.
Figure 17B:
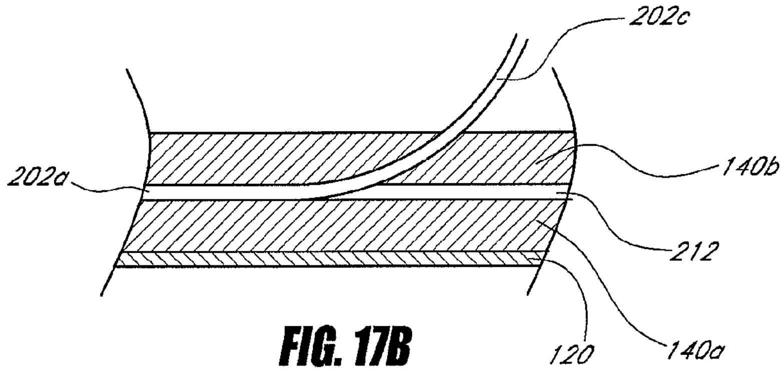
Figure 17C:
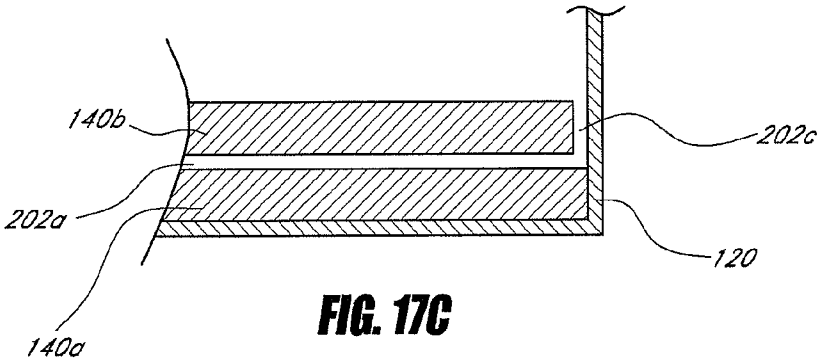

FIG. 17A schematically illustrates a cross-sectional view of an example main channel 202*a* and upward channel 202*c*. The upward channel 202*c* extends from the main channel 202*a* in a generally vertical direction through a portion of the culture medium 140, ending in the region of the volume 130 above the culture medium 140. FIG. 17B schematically illustrates a cross-sectional view of another example main channel 202*a* and upward channel 202*c*. In certain embodiments, the main channel 202*a* and the upward channel 202*c* are contiguous portions of the same elongate tubular structure. FIG. 17C schematically illustrates a cross-sectional view of another example main channel 202*a* and upward channel 202*c*. The upward channel 202*c* comprises a region between the culture medium 140 and an inner surface of the housing 120. Other configurations or directions of the upward channel 202*c* are also compatible with certain embodiments described herein.

The one or more ports 150 of certain embodiments are configured to provide access to the volume 130 without introducing other microbes, micro-organisms, or other contaminants into the volume 130. For example, the one or more ports 150 can be used to introduce a biological specimen into the volume 130, to apply suction to the volume 130, or to remove material (e.g., a portion of the cultured colony) from the volume 130 for additional study.

Figure 18A:
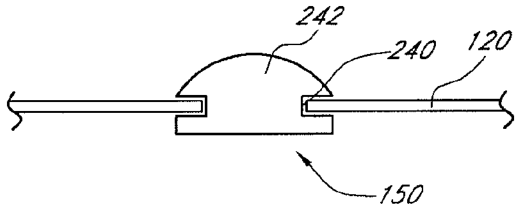
FIG. 18A schematically illustrates a cross-sectional view of an example port in accordance with certain embodiments described herein.
Figure 18B:
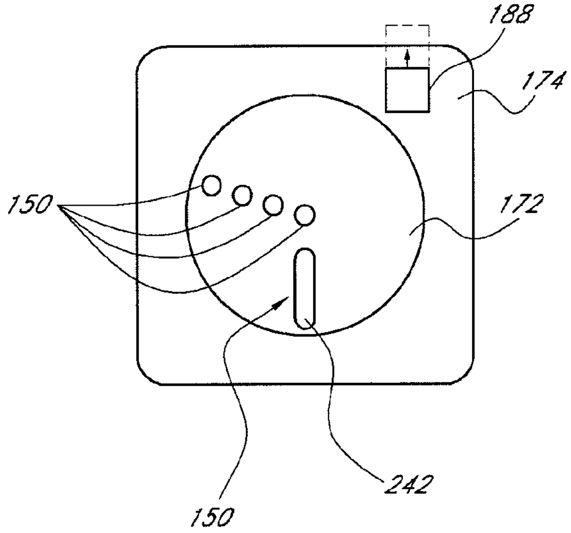
FIG. 18B schematically illustrates a top view of an example plurality of ports in accordance with certain embodiments described herein.

FIG. 18A schematically illustrates a cross-sectional view of an example port 150 in accordance with certain embodiments described herein. The port 150 in certain embodiments comprises a hole 240 through the housing 120 and an insert 242 within the hole 240. The insert 242 is configured to seal the hole 240 against passage of biological materials between the volume 130 and the environment 110 outside the device 100. In certain embodiments, the insert 242 is further configured to seal the hole 240 against passage of gas between the volume 130 and the environment 110 outside the device 100.

In certain embodiments, the insert 242 is removable from the hole 240 and reattachable to the hole 240, thereby providing access to the volume 130 (e.g., to introduce a biological specimen to the volume 130 or to remove a sample of a pathogen colony). In certain such embodiments, the port 150 is positioned on a top portion (e.g., lid) of the housing 120 or on a side portion of the housing 120. The insert 242 of certain such embodiments comprises a resilient material (e.g., neoprene, polyurethane, or another elastomer).

In certain other embodiments, the insert 242 is configured to be non-removable from the hole 240 and to be penetrated by a needle having a lumen therethrough (e.g., a sterile syringe needle 234), thereby providing access to the volume 130 (e.g., to introduce a biological specimen to the volume 130 or to remove a sample of a pathogen colony). The insert 242 is further configured to reseal itself upon removal of the needle 234 from the insert 242. In certain embodiments, the insert 242 comprises an elastomer material (e.g., neoprene or silicone). In certain embodiments, the port 150 comprises a plastic membrane which is pierced by a needle to access the volume 130.

In certain embodiments, the port 150 comprises a connector (e.g., a Luer-Lok® connector available from Becton, Dickenson and Company of Franklin Lakes, N.J.) and a blunt needle extending through the insert 242 and in fluid communication with the connector. In certain such embodiments, to introduce a liquid specimen through the port 150, a cap can be removed from the connector and a syringe can be coupled to the connector to inject the liquid specimen through the blunt needle. After the liquid specimen is introduced into the volume 130 through the port 150, the syringe can be removed, pulling the blunt needle with it and out of the port 150. The port 150 can self-seal upon removal of the blunt needle.

Certain such embodiments advantageously avoid using a sharp needle so as to minimize the risk of accidental punctures of the user.

In certain embodiments, the port 150 is positioned so that selected portions of the volume 130 are accessible via the port 150. For example, FIG. 18B schematically illustrates a top view of an example plurality of ports 150 in accordance with certain embodiments described herein. Each port 150 shown in FIG. 18B has a generally circular shape and is penetratable by a needle. The regions of the first portion 172 between the ports 150 can serve as viewing portions 188. In certain other embodiments, a port 150 has a generally elongate shape. In addition, in certain embodiments in which the port 150 is positioned on the first portion 172 of the housing 120 with the first portion 172 rotatable relative to the second portion 174 of the housing 120, the first portion 172 can be rotated so that the port 150 provides access to any selected portion of the volume 130. In certain such embodiments, the entire top surface of the culture medium 140 within the volume 130 is accessible from the port 150.

Figure 18C:
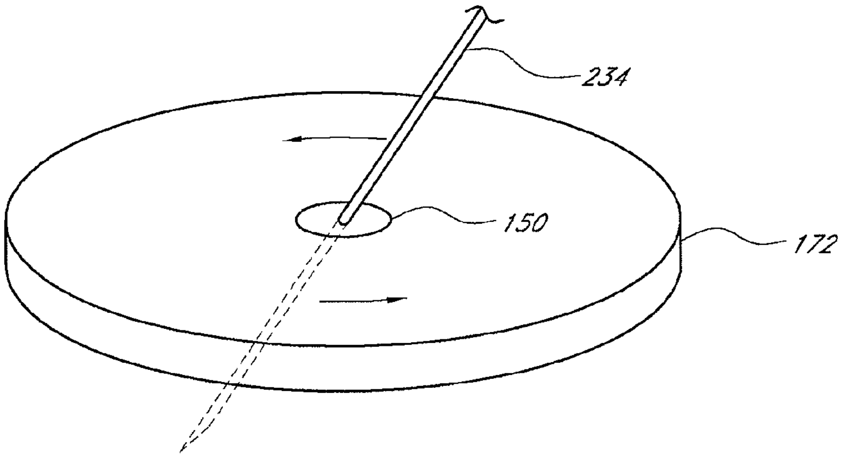
FIG. 18C schematically illustrates a perspective view of an example port on a first portion of the housing with a syringe needle extending through the port in accordance with certain embodiments described herein.

FIG. 18C schematically illustrates a perspective view of an example port 150 on a first portion 172 of the housing 120 with a syringe needle 234 extending through the port 150 in accordance with certain embodiments described herein. The needle 234 can be used to spray a liquid specimen into the volume 130 so that the liquid sample is on top of the culture medium 140. In certain embodiments, by inserting the needle 234 along a direction perpendicular to the first portion 172 of the housing 120 (e.g., vertically) and turning the needle 234 at an angle, as schematically illustrated by FIG. 18C, the needle 234 can spray the liquid specimen over a larger portion of the culture medium 140.

Figure 18D:
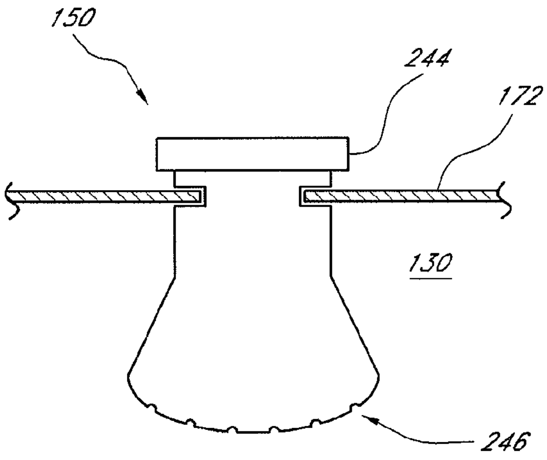
FIG. 18D schematically illustrates a cross-sectional view of another example port on a first portion of the housing in accordance with certain embodiments described herein.

FIG. 18D schematically illustrates a cross-sectional view of another example port 150 on a first portion 172 of the housing 120 in accordance with certain embodiments described herein. The port 150 comprises a connector 244 outside the volume 130 and a plurality of openings 246 inside the volume 130 and in fluidic communication with the connector 244. The connector 244 (e.g., a Luer-Lok® connector available from Becton, Dickenson and Company of Franklin Lakes, N.J.) of certain embodiments is configured to mate with a syringe (not shown). The openings 246 are configured to spray the liquid specimen into the volume 130 over an area of the top surface of the culture medium 140. Other configurations of the port 150 are also compatible with certain embodiments described herein. In certain embodiments, the port 150 shown in FIG. 18D is used to introduce the liquid specimen to a top surface of the culture medium 140 while another port 150 is used to introduce the liquid specimen below the top surface of the culture medium 140.

Figure 19:
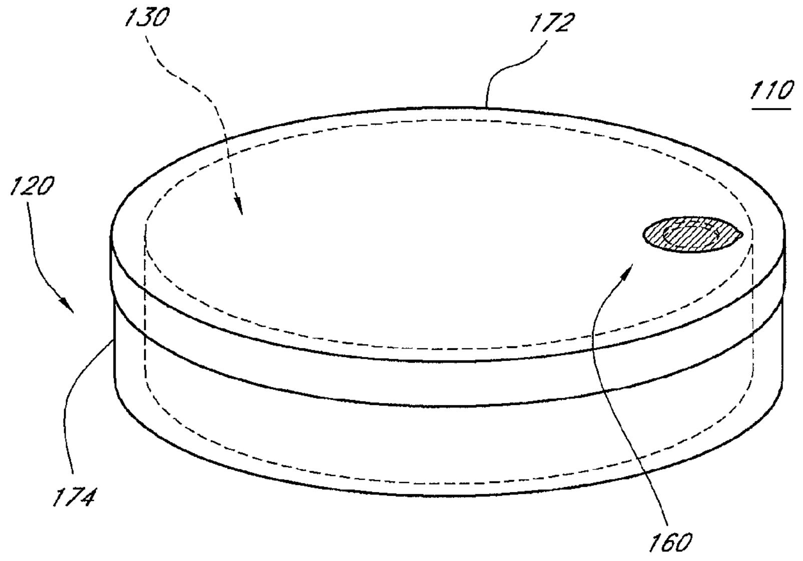
FIG. 19 schematically illustrates a perspective view of an example valve on a portion of the housing in accordance with certain embodiments described herein.

FIG. 19 schematically illustrates a perspective view of an example valve 160 on a portion of the housing 120 in accordance with certain embodiments described herein. The valve 160 is in fluidic communication with the volume 130 and the environment 110 outside the device 100. The valve 160 is configured to control transfer of gas between the volume 130 and the environment 110. For example, in certain embodiments, the valve 160 is responsive to a pressure within the volume 130 larger than a pressure of the environment 110 outside the device 100 by allowing gas from within the volume 130 to flow to the environment 110 outside the device 100, thereby reducing the pressure within the volume 130. In certain embodiments, the valve 160 has an open state and a closed state. In the open state, the valve 160 allows gas to flow from within the volume 130 to the environment 110 outside the device 100. In the closed state, the valve 160 inhibits gas from flowing between the volume 130 and the environment 110. The valve 160 switches from the closed state to the open state in response to a pressure within the volume 130 larger than a pressure of the environment 110 outside the device 100.

The valve 160 can be located on various portions of the housing 120. For example, in certain embodiments, the valve 160 is located on a first portion 172 of the housing 120, as schematically illustrated by FIG. 19. While the valve 160 is shown to be on a top wall of the first portion 172, in certain other embodiments, the valve 160 is located on a side wall of the first portion 172. In certain other embodiments, the valve 160 is located on a wall of the second portion 174 of the housing 120.

In certain embodiments, the valve 160 (e.g., a flapper valve) comprises a hole 260 through the housing 120 and a flexible member 262 (e.g., a flap) covering the hole 260. The hole 260 can be generally circular, generally oval, generally square, generally rectangular, or any other shape. In certain embodiments, the physical dimensions of the hole 260 are proportional to the volume 130 of the device 100 to be vented. In certain embodiments, the flexible member 262 comprises a plastic layer which is generally impermeable to gases penetrating therethrough. A first portion of the flexible member 262 is configured to remain stationary (e.g., affixed to the housing 120) during operation of the device 100 and a second portion of the flexible member 262 is configured to move (e.g., affixed or not affixed to the housing 120) during operation of the device 100.

Figure 20A:
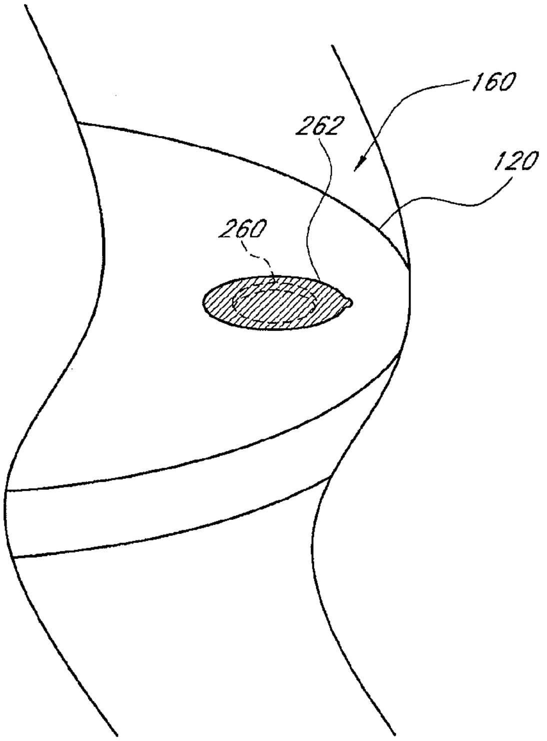
FIGS. 20A and 20B schematically illustrate two perspective views of an example valve in two positions in accordance with certain embodiments described herein.
Figure 20B:
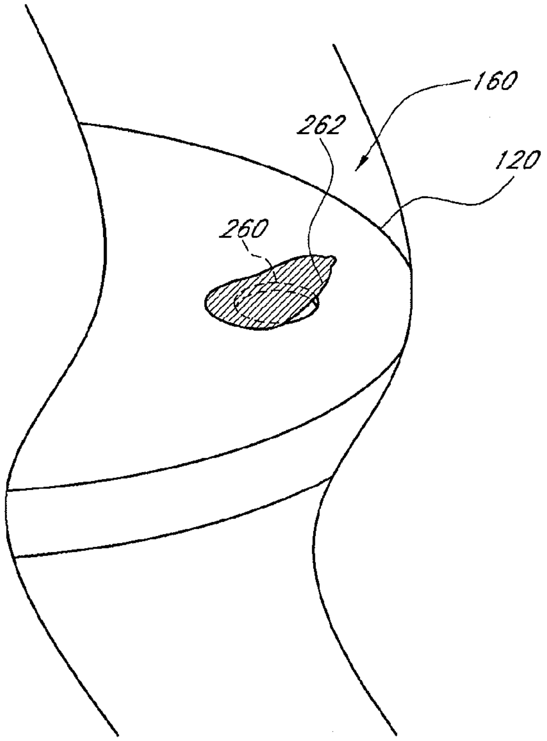

FIGS. 20A and 20B schematically illustrate two perspective views of an example valve 160 in two positions in accordance with certain embodiments described herein. The flexible member 262 is responsive to a pressure differential across the flexible member 262 (e.g., the pressure within the volume 130 being higher than the pressure outside the volume 130) by moving from a first position (e.g., closed, as shown in FIG. 20A) to a second position (e.g., open as shown in FIG. 20B). When in the first position, the flexible member 262 forms a seal around the hole 260 and prevents gas from flowing out of the volume 130 through the hole 260. When in the second position, at least a portion of the flexible member 262 is spaced from the housing 120 such that the flexible member 262 allows gas to flow out of the volume 130 through the hole 260. In certain embodiments, the flexible member 262 is configured to return to the first position after the pressure within the volume 130 is reduced. For example, when the pressure differential force is less than a restoring force (e.g., a force in an opposite direction to the bending of the flexible member 262), the restoring force moves the flexible member 262 back to the first position. When the pressure differential across the flexible member 262 is in the opposite direction (e.g., the pressure within the volume 130 being lower than the pressure outside the volume 130), the flexible member 262 remains sealed against the housing 120 such that the valve 160 inhibits flow of gas through the valve 160.

In certain embodiments, the valve 160 advantageously avoids significant increases of the pressure within the volume 130 (e.g., due to increased temperature within the volume 130 or due to gas released by the pathogen culture). For example, because the volume 130 is sealed, assembly of the device 100 can result in a pressure within the volume 130 which is higher than atmospheric pressure. This increased pressure at the ports 150 would effectively oppose introduction of the liquid specimen into the volume 130. The valve 160 of certain embodiments described herein advantageously is means for reducing the pressure within the volume 130 sufficiently so that the liquid specimen can be easily introduced into the volume 130, thereby facilitating use of the device 100. In certain embodiments, the valve 160 advantageously maintains a relatively constant pressure within the volume 130 by allowing excessive gas to escape. By responding to increased pressure within the volume 130, certain embodiments described herein allow the pressures inside the housing 120 and outside the housing 120 to equilibrate.

Figure 21:
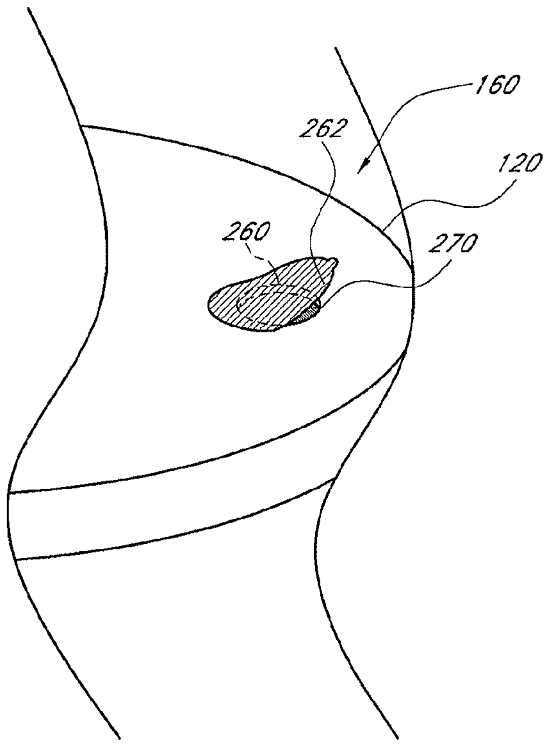
FIG. 21 schematically illustrates a perspective view of an example valve comprising a filter in accordance with certain embodiments described herein.

In certain embodiments, the valve 160 further comprises a filter 270 configured to inhibit contaminants from passing through the valve 160 while allowing one or more gases to flow therethrough. FIG. 21 schematically illustrates a perspective view of an example valve 160 comprising a filter 270 in accordance with certain embodiments described herein. For example, in certain embodiments as schematically illustrated by FIG. 21, the filter 270 covers the hole 260 and allows one or more gases (e.g., air, moisture) to escape the volume 130 within the housing 120 when the valve 160 is open without allowing contaminants (e.g., bacteria, fungi) to enter the volume 130. The filter 270 of certain embodiments comprises a micro-permeable membrane which allows gas exchange but prevents contamination. One example material for the filter 270 compatible with certain embodiments described herein is Breathe-Easy polymer-type membrane manufactured by Diversified Biotech of Boston, Mass. In various embodiments, the filter 270 can be positioned on an outer surface of the housing 120, on an inner surface of the housing 120, or within the hole 260 of the valve 160.

In certain embodiments, the filter 270 is differentially permeable such that it is configured to inhibit at least a first gas from flowing therethrough while allowing at least a second gas to flow therethrough. For example, the filter 270 of certain embodiments can discriminate between various atmospheric gases and water vapor, thereby increasing or decreasing the humidity within the volume 130. As another example, the filter 270 of certain embodiments can discriminate between oxygen and other gases, thereby maintaining, facilitating, or retarding an anaerobic or other specialized atmospheric condition within the volume 130.

In certain embodiments, the filter 270 is sealed with a protective, substantially impermeable plastic layer prior to use. The plastic layer can serve in certain embodiments as the flexible member 262. In certain such embodiments, a user places the device 100 in condition for use by peeling a portion of the plastic layer away from the housing 120, releasing a strong seal between the plastic layer and the housing 120 and allowing the plastic layer to return to its sealed position but only slightly resting on the housing 120, to allow the plastic layer to respond to pressure differentials between the volume 130 and the environment 110 by moving to either open or close the valve 160. In certain such embodiments, the plastic layer has a small tab to facilitate the user peeling the plastic layer back. In certain embodiments, the flexible member 262 can remain in place allowing venting of the volume 130 while facilitating anaerobic or microaerophilic growth conditions in the device 100. In addition, the flexible member 262 can be completely removed from the device 100, thereby leaving the hole 260 covered with the filter 270, which can be configured to allow oxygen to flow therethrough, thereby facilitating aerobic growth conditions within the volume 130. Alternatively, in certain embodiments, the flexible member 262 is configured to be closed during growth within the volume 130, thereby facilitating anaerobic growth conditions within the volume 130.

Figure 22A:
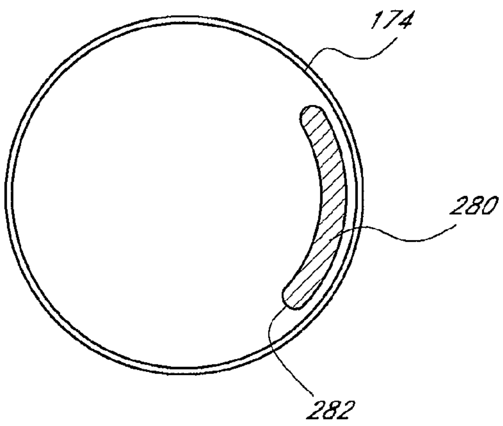
FIG. 22A schematically illustrates a top view of a bottom portion of the housing comprising the moisture absorbent material in accordance with certain embodiments described herein.

In certain embodiments, the device 100 comprises a moisture absorbent material 280 (e.g., foam, sponge, or other porous material) within the volume 130 and configured to receive moisture condensed onto an inner surface 190 of the housing 120 (e.g., on the viewing portion 188). FIG. 22A schematically illustrates a top view of a second portion 174 of the housing 120 comprising the moisture absorbent material 280 in accordance with certain embodiments described herein. The moisture absorbent material 280 is positioned in a recess or trough 282 (e.g., within and along at least one inner surface of the housing 120) to receive condensation flowing off the inner surface 190 of the housing 120 (e.g., the inner surface of the first portion 172 of the housing 120). In certain embodiments, the moisture absorbent material 280 is positioned below a lower portion of a sloping inner surface 190 of the housing 120 such that moisture moving along the sloping inner surface 190 forms droplets which fall onto the moisture absorbent material 280. In certain embodiments, the moisture absorbent material 280 is positioned below a portion of a plurality of ridges 192 along the inner surface 190 of the housing 120 such that moisture moving along the ridges 192 forms droplets which fall onto the moisture absorbent material 280. Certain embodiments advantageously provide the ability to collect the moisture in an accessible location such that the collected moisture can be sampled and tested for the presence of microorganisms (e.g., bacteria, viruses). For example, the device 100 can comprise a sliding or hinged viewing portion 188, as shown in FIG. 18B, to allow access to the moisture absorbent material 280 (e.g., to remove all or a portion of the moisture absorbent material 280 for analysis).

Figure 22B:
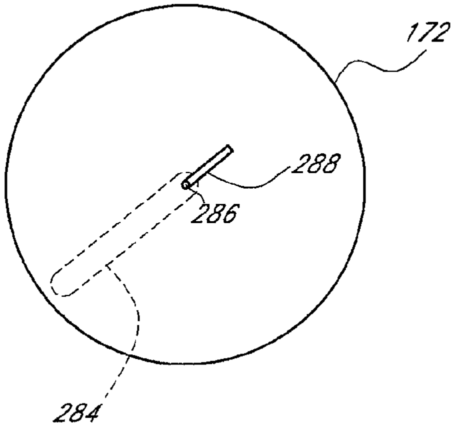
FIG. 22B schematically illustrates a top view of an example elongate member in accordance with certain embodiments described herein.

In certain embodiments, the device 100 comprises an elongate member 284 contacting the inner surface of the housing 120 and movable along the inner surface 190 to wipe moisture from at least a portion of the inner surface 190. In certain embodiments, the elongate member 284 facilitates removal of moisture from the inner surface 190 of the housing 120. For example, in certain embodiments, the elongate member 284 comprises the moisture absorbent material 280. FIG. 22B schematically illustrates a top view of an example elongate member 284 in accordance with certain embodiments described herein. The elongate member 284 contacts and extends along a portion of the inner surface of the first portion 172 of the housing 120. In certain such embodiments, the elongate member 284 comprises a rubber blade or a foam roll configured to push moisture along the inner surface of the first portion 172 of the housing 120. In certain embodiments, the elongate member 284 is rotatable about an axis 286 and has an extension 288 which a user can move so that the elongate member 284 wipes the inner surface of the first portion 172 of the housing 120, clearing it of moisture.

Figure 22C:
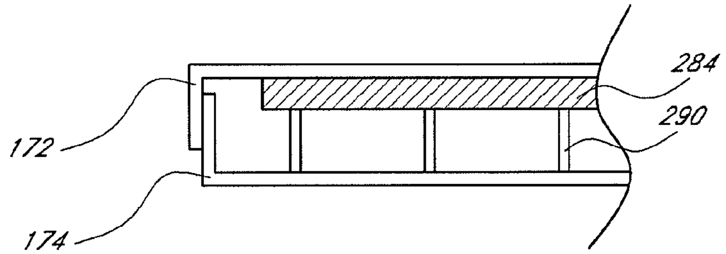
FIG. 22C schematically illustrates a cross-sectional view of another example elongate member in accordance with certain embodiments described herein.

FIG. 22C schematically illustrates a cross-sectional view of another example elongate member 284 in accordance with certain embodiments described herein. The elongate member 284 (e.g., rubber blade or foam roll) is fixed to the second portion 174 of the housing 120 (e.g., by one or more supports 290) and contacts the inner surface of the first portion 172 of the housing 120. In certain embodiments in which the first portion 172 is rotatable relative to the second portion 174, the elongate member 284 is movable along the inner surface of the first portion 172 to wipe moisture from at least a portion of the inner surface. In certain embodiments, the elongate member 284 comprises the moisture absorbent material 280.

Figure 23:
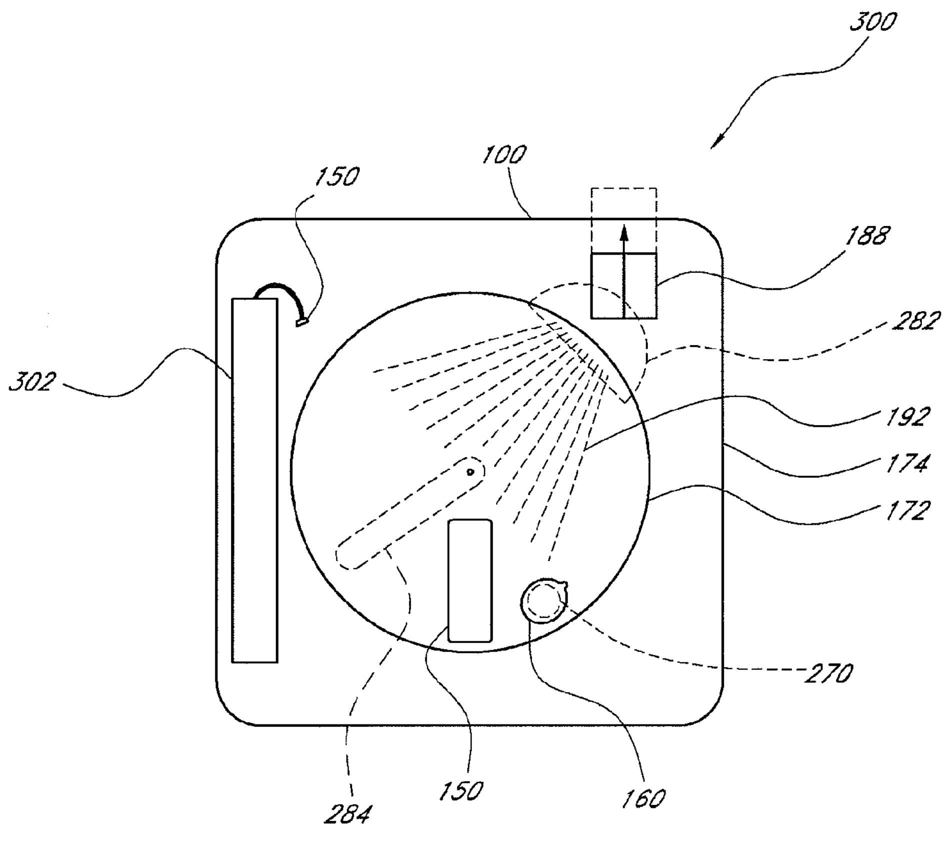
FIG. 23 schematically illustrates a top view of an example kit comprising the device in accordance with certain embodiments described herein.

FIG. 23 schematically illustrates a top view of an example kit 300 comprising the device 100 in accordance with certain embodiments described herein. In certain embodiments, the kit 300 comprises all of the components of the device 100 in a single package. As schematically illustrated by FIG. 23, the second portion 174 of the housing 120 has a generally square or rectangular profile, and the first portion 172 of the housing 120 has a generally circular profile. The first portion 172 fits onto a circular ridge of the second portion 174 to form the sealed volume 130. The first portion 172 of FIG. 23 has a port 150 for providing access to the volume 130 and a valve 160 and a filter 270 for controlling the pressure within the volume 130 as described herein. The first portion 172 of FIG. 23 also has an elongate member 284 in contact with the inner surface of the first portion 172 to wipe moisture away from the inner surface.

One corner of the second portion 174 comprises a trough 282 containing the moisture absorbent material 280 therein. The first portion 172 of the housing 120 is rotatable relative to the second portion 174 of the housing 120 and the first portion 172 comprises a plurality of ridges 192 along the inner surface 190 of the first portion 172. When the first portion 172 is in a first position (e.g., a "home" position), at least a portion of the plurality of ridges 192 extend over the trough 282 such that condensation can flow along the ridges 192 to drop onto the moisture absorbent material 280. The first portion 172 of the housing 120 comprises a viewing portion 188 having a sliding plastic window to allow access to the moisture absorbant material 280. The kit 300 of certain embodiments further comprises a vacuum source 302 (e.g., Vacutainer®) on one side of the kit 300 configured to be placed in fluidic communication with the volume 130 via a port 150 on the second portion 174. In certain embodiments, the second portion 174 extends beyond the first portion 172 to provide support for various other components of the kit 300 (e.g., vacuum source 302, trough 282).

Figure 24:
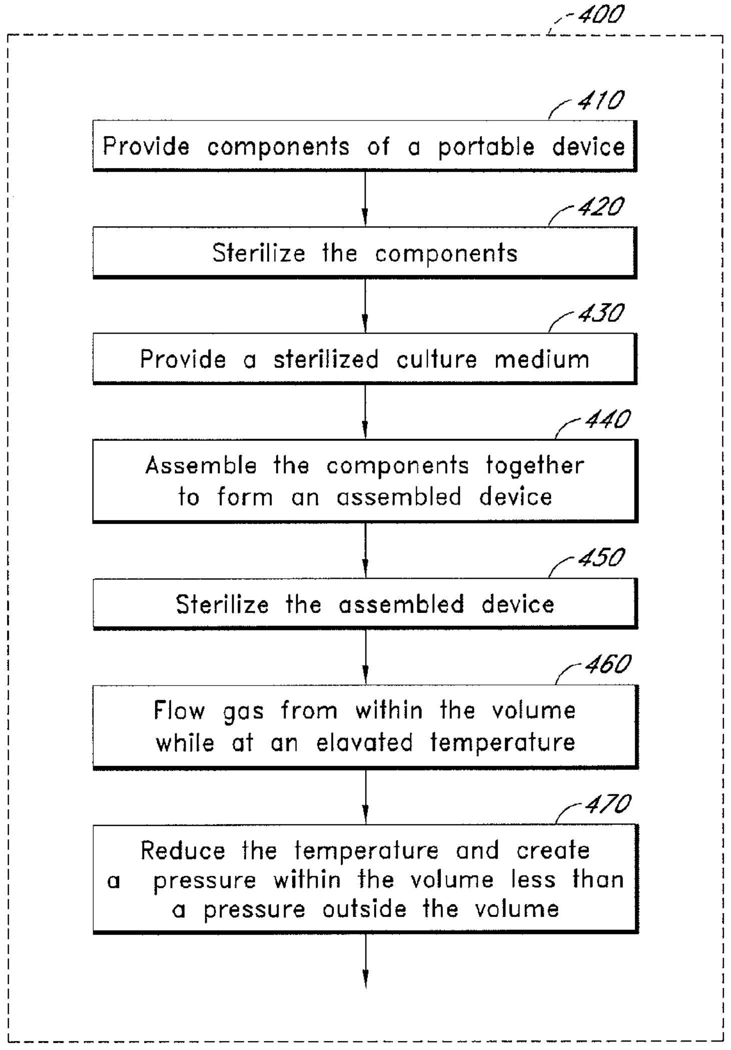
FIG. 24 is a flowchart of an example method of providing portable biological testing capabilities in accordance with certain embodiments described herein.

In the following description of various methods in accordance with certain embodiments described herein, reference is made to various components of the device 100 as described above. However, in accordance with certain embodiments, the methods described herein can be used with other components and other devices with other structures than those described above. In addition, while the methods are described below with operational blocks in particular sequences, other FIG. 24 is a flowchart of an example method 400 of providing portable biological testing capabilities in accordance with certain embodiments described herein. The method 400 advantageously provides these biological testing capabilities free from biological contamination from a local environment. In an operational block 410, the method 400 comprises providing components of a portable device 100. The components are configured to be assembled together to seal a volume 130 within the device 100 against passage of biological materials between the volume 130 and an environment 110 outside the device 100. In an operational block 420, the method 400 further comprises sterilizing the components. In an operational block 430, the method 400 further comprises providing a sterilized culture medium 140. In an operational block 440, the method 400 further comprises assembling the components together with the sterilized culture medium 140 within the volume 130, thereby forming an assembled device 100. In an operational block 450, the method 400 further comprises sterilizing the assembled device 100. Sterilizing the assembled device 100 comprises elevating a temperature of the assembled device 100. In an operational block 460, the method 400 further comprises flowing gas from within the volume 130 to the environment 110 while the assembled device 100 is at an elevated temperature. In an operational block 470, the method 400 further comprises reducing the temperature of the assembled device 100 to be less than the elevated temperature while preventing gas from flowing from the environment 110 to the volume 130. A pressure is created within the volume 130 which is less than a pressure outside the volume 130. In certain other embodiments, the method 400 includes other operational blocks and/or has other sequences of operational blocks.

In certain embodiments, providing components of a portable device 100 in the operational block 410 comprises providing a portable housing 120, a sealed volume 130 surrounded by the housing 120, one or more ports 150 configured to provide access to the volume 130, and a valve 160 in fluidic communication with the volume 130 and the environment 110. Devices 100 comprising other sets of components are also compatible with certain embodiments described herein. In certain embodiments, providing the components in the operational block 410 further comprises providing a culture medium 140. In certain such embodiments, sterilizing the components in the operational block 420 comprises sterilizing the culture medium 140. Thus, providing a sterilized culture medium 140 in the operational block 430 is performed as part of the operational blocks 410 and 420.

In certain embodiments, sterilizing the components in the operational block 420 comprises heating the components. In certain other embodiments, sterilizing the components comprises exposing the components to gamma radiation or ultraviolet radiation. Similarly, in certain embodiments, sterilizing the assembled device 100 in the operational block 450 comprises heating the assembled device 100. In certain other embodiments, sterilizing the assembled device 100 comprises exposing the assembled device 100 to gamma radiation or ultraviolet radiation. In certain embodiments, exposing the assembled device 100 to gamma or ultraviolet radiation elevates the temperature of the assembled device 100. In certain embodiments, the elevated temperature is greater than a temperature of the assembled device 100 prior to being sterilized.

In certain embodiments in which the device 100 comprises a valve 160 as described herein (e.g., a one-way valve or flapper valve), elevating the temperature of the assembled device 100 in the operational block 450 causes gas to flow from within the volume 130 to the environment 110. Thus, in certain such embodiments, the operational block 460 is performed as part of the operational block 450. Furthermore, in certain such embodiments, reducing the temperature of the assembled device 100 to be less than the elevated temperature in the operational block 470 causes the pressure within the volume 130 to be less than a pressure outside the volume 130. Similarly, in certain embodiments in which the device 100 comprises a valve 160 as described herein, the valve 160 closes once there is no longer a pressure differential force keeping the valve 160 open. Since the closed valve 160 prevents gas from flowing from the environment 110 to the volume 130, reducing the temperature of the assembled device 100 after the valve 160 is closed results in the pressure of the volume 130 reducing to be less than a pressure in the environment 110 outside the volume 130.

Certain embodiments described herein advantageously provide a device 100 having a sterilized volume 130 with a reduced pressure therein. The device 100 of certain such embodiments can be shipped while having the reduced pressure in the volume 130, thereby relieving the end user from having to create the reduced pressure in the volume 130. In addition, certain such embodiments advantageously create the reduced pressure during the sterilization process, thereby reducing the number of steps needed to provide the device 100.

In certain embodiments, the method 400 further comprises providing a desiccant material (e.g., calcium carbonate) and placing the assembled device 100 and the desiccant material within a container (e.g., a plastic bag), and sealing the container against passage of biological materials and water vapor between the assembled device and a region outside the container. The container of certain embodiments is generally impermeable to biological materials and water vapor penetrating therethrough. In certain such embodiments, sterilizing the assembled device in the operational block 450 is performed while the assembled device 100 is sealed within the container. In certain embodiments, the desiccant material advantageously absorbs water vapor within the container (e.g., plastic bag), including water vapor emitted from the device 100 while the device 100 is being sterilized (e.g., by gamma radiation).

Figure 25:
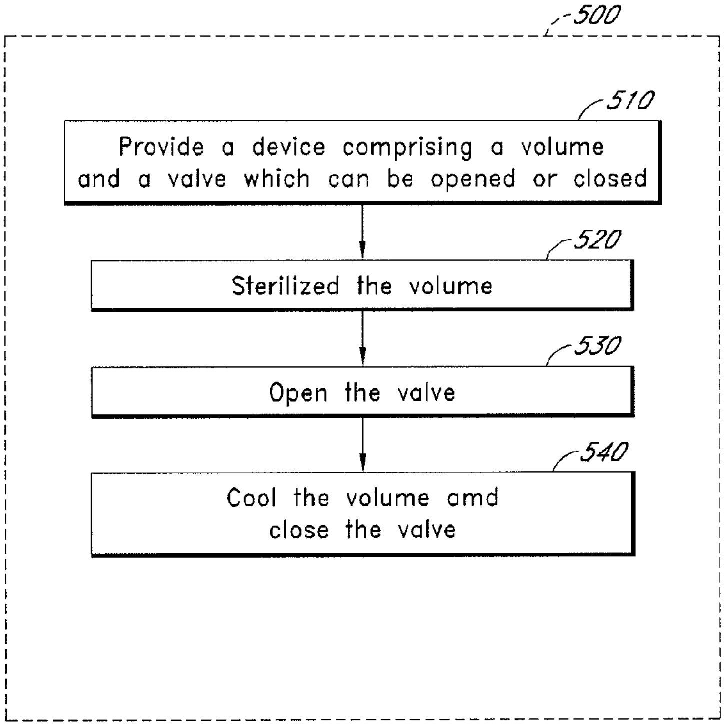
FIG. 25 is a flowchart of an example method of providing a sterilized volume with a reduced pressure in accordance with certain embodiments described herein.

FIG. 25 is a flowchart of an example method 500 of providing a sterilized volume 130 with a reduced pressure in accordance with certain embodiments described herein. In an operational block 510, the method 500 comprises providing a device 100. The device 100 comprises a volume 130 sealed against passage of biological material between the volume 130 and a region outside the volume 130. The device 100 further comprises a valve 160 which can be closed or opened. The valve 160 inhibits gas from flowing from the region to the volume 130 when closed. The valve 160 allows gas to flow from the volume 160 to the region when opened. The valve 160 opens in response to a pressure within the volume 130 being greater than a pressure within the region. In an operational block 520, the method 500 further comprises sterilizing the volume 130. Sterilizing the volume 130 increases the temperature within the volume 130 and increases the pressure within the volume 130 to be greater than the pressure within the region. In an operational block 530, the method 500 further comprises opening the valve 160 in response to the increased pressure within the volume 130, thereby allowing gas to flow through the valve 160 from the volume 130 to the region. In an operational block 540, the method 500 further comprises cooling the volume 130 and closing the valve 160. Cooling the volume 130 decreases the pressure within the volume 130 to create a pressure differential across the valve 160. In certain other embodiments, the method 500 includes other operational blocks and/or has other sequences of operational blocks.

In certain embodiments in which the device 100 comprises a valve 160 as described herein (e.g., a one-way valve or flapper valve), sterilizing the volume 130 (e.g., by irradiating the volume 130 with gamma radiation or ultraviolet radiation) and increasing the temperature within the volume 130 in the operational block 520 increases the pressure within the volume 130, thereby causing the valve 160 to open and gas to flow from within the volume 130 to the region outside the volume 130. Thus, in certain such embodiments, the operational block 530 is performed as part of the operational block 520. Furthermore, in certain such embodiments, the valve 160 closes once the pressure within the volume 130 and outside the volume 130 equilibrizes. Cooling the volume 130 in conjunction with the closed valve 160 in the operational block 540 causes the pressure within the volume 130 to be less than a pressure outside the volume 130 since the closed valve 160 prevents gas from flowing from the region outside the volume 130 to within the volume 130. Thus, a pressure differential across the valve 160 is formed.

Figure 26:
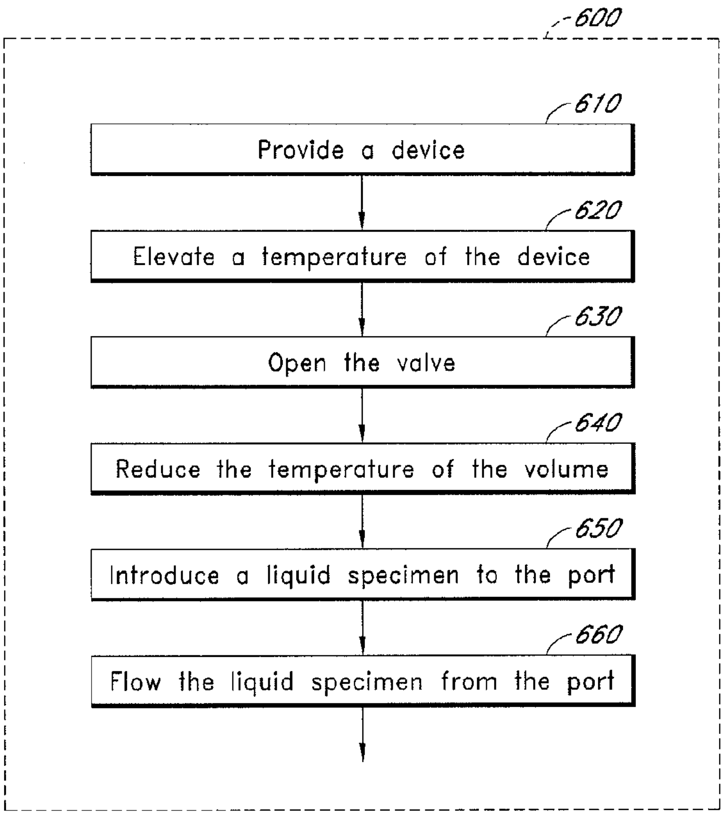
FIG. 26 is a flowchart of an example method of using a biological testing device in accordance with certain embodiments described herein.

FIG. 26 is a flowchart of an example method 600 of using a biological testing device 100 in accordance with certain embodiments described herein. In an operational block 610, the method 600 comprises providing a device 100 comprising a housing 120 and a volume 130 surrounded by the housing 120 and sealed against passage of biological materials between the volume 130 and the environment 110 outside the device 100. The device 100 further comprises a culture medium 140 within the volume 120 and a port 150 configured to provide access to the volume 130 while avoiding biological contamination of the volume 130. The device 100 further comprises one or more channels 202 within the volume 130. The one or more channels 202 are in fluidic communication with the port 150, with the culture medium 140, and with a region of the volume 130 above the culture medium 140. The device 100 further comprises a valve 160 in fluidic communication with the volume 130 and the environment 110. The valve 160 has an open state and a closed state. In the open state, gas flows from within the volume 130 to the environment 110 outside the device 100. In the closed state, gas is inhibited from flowing between the volume 130 and the environment 110. The valve 160 is in the open state in response to a pressure within the volume 130 larger than a pressure of the environment 110 outside the device 100, thereby reducing the pressure within the volume 130.

In an operational block 620, the method 600 further comprises elevating a temperature of the volume 130. In an operational block 630, the method 600 further comprises opening the valve 160 while the volume 130 is at an elevated temperature. In an operational block 640, the method 600 further comprises reducing the temperature of the volume 130 while the valve 160 is closed, thereby reducing a pressure within the volume 130. In an operational block 650, the method 600 further comprises introducing a liquid specimen to the port 150 at an inlet pressure. In an operational block 660, the method 600 further comprises flowing the liquid specimen from the port 150, through the one or more channels 202, to the culture medium 140. Flowing of the liquid specimen is facilitated by a pressure differential force between the inlet pressure at the port 150 and the reduced pressure within the volume 130. In certain other embodiments, the method 600 includes other operational blocks and/or has other sequences of operational blocks.

In certain embodiments, the liquid specimen comprises blood, blood components, pus, urine, mucus, feces, microbes obtained by throat swab, sputum, cerebrospinal fluid, or other biological material from a patient to be diagnosed. The port 150 can be configured to receive a needle comprising a lumen (e.g., a syringe needle or blunt needle as described herein) through which the liquid specimen is delivered to the volume 130. For example, the port 150 can provide access through the housing 120 into the volume 130, as described herein. In certain embodiments, the port 150 is in fluidic communication with the one or more channels 202, as described herein. For example, the port 150 can be configured to be penetrated by the needle to introduce the liquid specimen to the volume 130 and to reseal itself upon removal of the needle from the port 150. In certain embodiments, the port 150 comprises an access portion 228 within the volume 130 and in fluidic communication with the one or more channels 202. In certain such embodiments, the access portion 228 provides fluidic access to the channels 202 such that a liquid specimen introduced to the access portion 228 flows through the channels 202 to be distributed along the culture medium 140. As described herein, in certain embodiments, the one or more channels 202 provides fluidic communication between the port 150 and the region of the volume 130 above the culture medium 140. Thus, a difference in pressure between the port 150 and the region of the volume 130 above the culture medium 140 creates a pressure differential force on the liquid specimen which facilitates the flow of the liquid specimen through the one or more channels 202. Since in certain embodiments the one or more channels 202 comprise a plurality of orifices 214 in fluidic communication with the culture medium 140, the liquid specimen flowing through the one or more channels 202 is distributed across the culture medium 140.

In certain embodiments, the liquid specimen is introduced to the port 150 at an inlet pressure greater than or equal to atmospheric pressure. In certain other embodiments, the liquid specimen is introduced to the port 150 at an inlet pressure less than atmospheric pressure but greater than a pressure within the volume 130.

Certain embodiments described herein provide rapid and even distribution of the liquid specimen through the one or more channels 202. The liquid specimen can be rapidly distributed throughout the culture medium 140, facilitated at least in part by the pressure differential force between the volume 130 and the port 150 through which the liquid specimen is introduced to the volume 130.

In the use of standard laboratory culturing dishes (e.g., Petri dishes), culture media such as agar typically release moisture, and moisture and various gases are typically produced by the microbes grown on or in the culture medium. Because moisture is viewed as an enemy of growing discrete colonies (which is a fundamental goal of microbiology), Petri dishes are intended to allow this moisture to evaporate away from the dish and to allow the gases to escape the dish. Therefore, prior systems have not envisioned a purpose for a valve as described herein.

Petri dishes in incubators also have the possibility of cross contamination. In addition, the lids of Petri dishes are typically opened periodically to monitor the culture growing therein. These standard laboratory methods invite contamination, and complicated guidelines have been adopted to deal with reducing the likelihood of contamination, but some possibility of contamination remains. Standard practice now involves calling anything unexpected a contaminant.

Certain embodiments described herein advantageously provide a sealed volume 130 which is sterilized after the device 100 is assembled and filled with the culture medium 140, ready for use. To sterilize the assembled device 100, radiation (e.g., gamma radiation or ultraviolet radiation) can be used, however, the sterilization process can create heat with consequent pressure differences between the volume 130 and outside the device 100, with resultant problems in use.

The valve 160 of certain embodiments described herein provides a means to control the internal pressure of the volume 130. The valve 160 of certain embodiments is automatic, sensitive to slight pressures, and sufficiently inexpensive to be used in a disposable device 100.

In certain embodiments in which the valve 160 comprises a plastic flapper valve, the device 100 advantageously provides both an aerobic and anaerobic test in one device 100. In certain such embodiments, the flexible member 262 (e.g., flap) can be removed leaving the remaining filter 270 on the device 100. If the filter 270 is configured to allow oxygen to enter the volume 130, an aerobic condition can be created within the volume 130. If the flexible member 262 is left on the device 100, an anaerobic condition can be created within the volume 130. In certain other embodiments, this capability could be provided by a separate port dedicated for this purpose. Such capabilities are not provided by existing culturing dishes.

Certain embodiments described herein allow visualization of the various cultured colonies within the device 100. In addition, certain embodiments described herein facilitate the visualization of the effects of various proposed drugs or other treatments on the cultured colonies. For example, the device 100 of certain embodiments is ideally suited for typical Kirby-Bauer diffusion tests in which small samples of various substances (e.g., drugs, reagents) are placed on filter paper discs or similar medium and are allowed to diffuse into the culture medium 140. In certain embodiments, the discs can be applied to the culture medium 140 using an assembly configured for this purpose, as described more fully in U.S. Pat. No. 6,204,056, which is incorporated in its entirety by reference herein. For example, a test grid assembly containing drug samples can be arranged within the device 100 and configured to be brought into contact with the culture medium 140 in corresponding partitioned regions 186 when desired. Alternatively, the plurality of channels 202 can be utilized to deliver a pattern of test substances in a predetermined pattern. Combinations of the assembly and plurality of channels 202 can be used to deliver a variety of test compounds to various portions of the culture medium 140 to mimic a complex treatment regime. Certain embodiments described herein advantageously allow a user to follow a series of relatively simple instructions without having to understand the underlying complexity.

Certain embodiments described herein, particularly in combination with the partitioned culture medium 140 described above, advantageously provide a simple way to interpret the results of the analysis. For example, in certain embodiments, the same liquid specimen can be introduced to each of the partitioned regions of the culture medium 140 and each partitioned region can be exposed to a different test substance or drug. In certain such embodiments, the appearance of the partitioned regions of the culture medium 140 can be indicative of the microorganisms (e.g., bacteria, viruses) in the liquid specimen and/or the efficacy of various drugs (e.g., antibiotics) on the microorganisms of the liquid specimen. In certain embodiments, the device 100 can be used with a listing of possible resulting patterns of the appearance of the partitioned regions of the culture medium 140 (e.g., clear regions, regions that show growth, regions that show a particular color resulting from interactions of pathogens and indicator substances). By matching the appearance of the device 100 to one of the patterns in the listing advantageously allows the user to make a complex diagnosis or determination using the device 100.

While the methods are described herein with reference to various configurations of the device 100 and its various components, other configurations of systems and devices are also compatible with embodiments of the methods described herein. Any method which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the method(s) described herein.

Certain aspects, advantages and novel features of the invention have been described herein. It is to be understood, however, that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. A method of providing portable biological testing capabilities free from biological contamination from a local environment, the method comprising:

providing components of a portable device, the components configured to be assembled together to seal a volume within the device against passage of biological materials between the volume and an environment outside the device;

sterilizing the components;

providing a sterilized culture medium;

assembling the components together with the sterilized culture medium within the volume, thereby forming an assembled device;

sterilizing the assembled device, wherein sterilizing the assembled device comprises elevating a temperature of the assembled device;

flowing gas from within the volume to the environment while the assembled device is at an elevated temperature due to said sterilizing the assembled device; and reducing the temperature of the assembled device to be less than the elevated temperature while preventing gas from flowing from the environment to the volume, thereby creating a pressure within the volume which is less than a pressure outside the volume.

2. The method of claim 1, wherein sterilizing the components comprises exposing the components to gamma radiation or ultraviolet radiation.

3. The method of claim 1, wherein sterilizing the assembled device comprises exposing the assembled device to gamma radiation or ultraviolet radiation.

4. The method of claim 1, further comprising:

providing a desiccant material;

placing the assembled device and the desiccant material within a container; and sealing the container against passage of biological materials and water vapor between the assembled device and a region outside the container, wherein sterilizing the assembled device is performed while the assembled device is sealed within the container.

5. The method of claim 1, wherein the assembled device comprises a valve in fluidic communication with the volume and the environment, wherein flowing gas from within the volume to the environment comprises opening the valve, and preventing gas from flowing from the environment to the volume comprises closing the valve.

6. The method of claim 5, wherein the valve opens in response to an elevated pressure within the volume and closes once there is no longer a pressure differential force keeping the valve open.

7. The method of claim 5, wherein the valve comprises a hole through a housing of the assembled device and a flexible layer covering the hole, wherein a portion of the flexible layer is configured to flex away from the hole in response to pressure within the volume being greater than pressure within the environment.

8. The method of claim 1, wherein the assembled device comprises a growth medium while the assembled device is being sterilized.

9. A method of providing a sterilized volume with a reduced pressure, the method comprising:

providing a device comprising:

a volume sealed against passage of biological material between the volume and a region outside the volume; and a valve which can be closed or opened, the valve inhibiting gas from flowing from the region to the volume when closed, the valve allowing gas to flow from the volume to the region when opened, wherein the valve opens in response to a pressure within the volume being greater than a pressure within the region;

sterilizing the volume, wherein said sterilizing increases a temperature within the volume and increases the pressure within the volume to be greater than the pressure within the region;

opening the valve in response to the increased pressure within the volume, thereby allowing gas to flow through the valve from the volume to the region; and cooling the volume and closing the valve, wherein said cooling decreases the pressure within the volume to create a pressure differential across the valve.

10. The method of claim 9, wherein sterilizing the volume comprises irradiating the volume with gamma radiation or ultraviolet radiation.

11. The method of claim 9, further comprising:

providing a desiccant material;

placing the device and the desiccant material within a container; and sealing the container against passage of biological materials and water vapor between the device and a region outside the container, wherein sterilizing the volume is performed while the device is sealed within the container.

12. The method of claim 9, wherein the valve comprises a hole through a housing of the device and a flexible layer covering the hole, wherein a portion of the flexible layer is configured to flex away from the hole in response to pressure within the volume being greater than pressure within the environment.

13. The method of claim 9, wherein the valve opens in response to an elevated pressure within the volume and closes once there is no longer a pressure differential force keeping the valve open.

14. The method of claim 9, wherein the device comprises a growth medium while the volume is being sterilized.

15. A method of using a biological testing device, the method comprising:

providing a device comprising:

a housing;

a volume surrounded by the housing and sealed against passage of biological materials between the volume and the environment outside the device;

a growth medium within the volume;

a port configured to provide access to the volume while avoiding biological contamination of the volume; and one or more channels within the volume, the one or more channels in fluidic communication with the port, with the culture medium, and with a region of the volume above the culture medium;

a valve in fluidic communication with the volume and the environment, the valve having an open state in which gas flows from within the volume to the environment outside the device and having a closed state in which gas is inhibited from flowing between the volume and the environment, wherein the valve is in the open state in response to a pressure within the volume larger than a pressure of the environment outside the device, thereby reducing the pressure within the volume;

elevating a temperature of the volume;

opening the valve while the volume is at an elevated temperature;

reducing the temperature of the volume while the valve is closed, thereby reducing a pressure within the volume;

introducing a liquid specimen to the port at an inlet pressure; and flowing the liquid specimen from the port, through the one or more channels, to the culture medium, wherein the flowing of the liquid specimen is facilitated by a pressure differential force between the inlet pressure at the port and the reduced pressure within the volume.

16. The method of claim 15, wherein elevating the temperature of the volume comprises sterilizing the volume.

17. The method of claim 16, wherein sterilizing the volume comprises exposing the volume to gamma radiation or ultraviolet radiation.

18. The method of claim 16, further comprising:

providing a desiccant material;

placing the volume and the desiccant material within a container; and sealing the container against passage of biological materials and water vapor between the volume and a region outside the container, wherein sterilizing the volume is performed while the volume is sealed within the container.

19. The method of claim 15, wherein the valve closes once there is no longer a pressure differential force keeping the valve open.

20. The method of claim 15, wherein the valve comprises a hole through the housing and a flexible layer covering the hole, wherein a portion of the flexible layer is configured to flex away from the hole in response to pressure within the volume being greater than pressure within the environment.

* * * * *